United States Patent
Jung et al.

(10) Patent No.: US 10,238,286 B2
(45) Date of Patent: Mar. 26, 2019

(54) METHOD AND DEVICE FOR RADIATING LIGHT USED TO CAPTURE IRIS

(71) Applicant: Samsung Electronics Co., Ltd., Suwon-si, Gyeonggi-do (KR)

(72) Inventors: Dae-kwang Jung, Suwon-si (KR); Jun-ho Koh, Suwon-si (KR); Byeong-hoon Kwak, Uiwang-si (KR); Sung-chan Kim, Suwon-si (KR); Yang-wook Kim, Hwaseong-si (KR); Chang-han Kim, Suwon-si (KR); Hyun-jung Kim, Suwon-si (KR); In-hak Na, Yongin-si (KR); Kang-jin Yoon, Seoul (KR); Yong-chan Lee, Seoul (KR); Jae-ho Jung, Yongin-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 495 days.

(21) Appl. No.: 14/960,828

(22) Filed: Dec. 7, 2015

(65) Prior Publication Data

US 2016/0262615 A1    Sep. 15, 2016

(30) Foreign Application Priority Data

Mar. 12, 2015    (KR) .................. 10-2015-0034522

(51) Int. Cl.
*G06K 9/00* (2006.01)
*G03B 15/02* (2006.01)
(Continued)

(52) U.S. Cl.
CPC .............. *A61B 3/14* (2013.01); *G03B 15/02* (2013.01); *G06K 9/00604* (2013.01); *H04N 5/2256* (2013.01); *A61B 3/1216* (2013.01)

(58) Field of Classification Search
CPC .............. G06K 9/00597; G02B 13/004; G02B 6/0068; F21V 14/06
(Continued)

(56) References Cited

U.S. PATENT DOCUMENTS 6,247,813 B1    6/2001    Kim et al.
6,542,624 B1    4/2003    Oda
(Continued)

FOREIGN PATENT DOCUMENTS

CN    101098407 A    1/2008
JP    2000-033080 A    2/2000
(Continued)

OTHER PUBLICATIONS

CN Office Action dated Oct. 19, 2018 issued in CN Application No. 201580077581.1.

*Primary Examiner* — William J Carter
(74) *Attorney, Agent, or Firm* — Jefferson IP Law, LLP

(57) ABSTRACT

A method and device for radiating light used to capture an iris are provided. The device for radiating light to capture an iris of a user includes a lens unit including a lens array of arranged lenses, a light source configured to radiate light beams into the iris of the user via the arranged lenses by emitting the light beams toward the arranged lenses, and a controller configured to change positions of the arranged lenses based on a distance between the device and the iris, in which the lens array is positioned between the light source and the iris.

18 Claims, 33 Drawing Sheets

(51) Int. Cl.
*A61B 3/14* (2006.01)
*H04N 5/225* (2006.01)
*A61B 3/12* (2006.01)

(58) Field of Classification Search
USPC .............................. 362/277, 281, 283, 332
See application file for complete search history.

(56) References Cited

U.S. PATENT DOCUMENTS

| | | |
|---|---|---|
| 6,594,377 B1 | 7/2003 | Kim et al. |
| 7,271,839 B2 | 9/2007 | Lee et al. |
| 2002/0130961 A1 | 9/2002 | Lee et al. |
| 2006/0088193 A1 | 4/2006 | Muller et al. |
| 2008/0002960 A1 | 1/2008 | Ito et al. |
| 2008/0247606 A1* | 10/2008 | Jelinek ............... G06K 9/00604 382/115 |
| 2010/0034529 A1 | 2/2010 | Jelinek |
| 2010/0128937 A1 | 5/2010 | Yoo et al. |
| 2010/0149073 A1* | 6/2010 | Chaum .............. G02B 27/0093 345/8 |
| 2013/0027944 A1 | 1/2013 | Hough et al. |
| 2013/0088584 A1 | 4/2013 | Malhas et al. |
| 2013/0088685 A1 | 4/2013 | Holland |
| 2015/0062324 A1 | 3/2015 | Choi |
| 2015/0196199 A1* | 7/2015 | Toda ................... A61B 3/1216 351/206 |

FOREIGN PATENT DOCUMENTS

| | | |
|---|---|---|
| JP | 2004164483 A | 6/2004 |
| WO | 2013/154273 A1 | 10/2010 |

\* cited by examiner

METHOD AND DEVICE FOR RADIATING LIGHT USED TO CAPTURE IRIS

CROSS-REFERENCE TO RELATED APPLICATION(S)

This application claims the benefit under 35 U.S.C. § 119(a) of a Korean patent application filed on Mar. 12, 2015 in the Korean Intellectual Property Office and assigned Serial number 10-2015-0034522, the entire disclosure of which is hereby incorporated by reference.

TECHNICAL FIELD

The present disclosure relates to a method and device for radiating light used to capture an iris. More particularly, the present disclosure relates to a method and device for radiating light into an iris by emitting a plurality of light beams to a plurality of arranged lenses.

BACKGROUND

As network and multimedia technologies have developed, it has become possible for a user to receive various services through a device. It has also become possible to use iris information of a user to authenticate the user when the user uses a service. In addition, an iris of a user may be captured to authenticate the user using iris information of the user, and an appropriate quantity of light may be radiated to the iris of the user in order to capture the iris of the user.

However, since light is not radiated into an iris of a user using multiple lenses, it is difficult to radiate light to the iris of the user while protecting an eye of the user according to the related art. In particular, it is more difficult to effectively radiate light into an iris of a user when the user is walking around or traveling in a vehicle.

Accordingly, a technique is needed to safely radiate light into an iris of a user using a plurality of lenses and adaptively radiate light into the iris of the user during movement.

The above information is presented as background information only to assist with an understanding of the present disclosure. No determination has been made, and no assertion is made, as to whether any of the above might be applicable as prior art with regard to the present disclosure.

SUMMARY

Aspects of the present disclosure are to address at least the above-mentioned problems and/or disadvantages and to provide at least the advantages described below. Accordingly, an aspect of the present disclosure is to provide a method and device for effectively radiating light into an iris of a user using a plurality of lenses, which are arranged.

Provided are a method and device for adjusting positions of the plurality of lenses on the basis of a distance between the device and the iris of the user.

Provided are a method and device for adjusting different quantities of light emitted to the plurality of lenses.

Additional aspects will be set forth in part in the description which follows and, in part, will be apparent from the description, or may be learned by practice of the presented various embodiments of the present disclosure.

In accordance with an aspect of the present disclosure, a device for radiating light to capture an iris of a user is provided. The device includes a lens unit including a lens array of arranged lenses, a light source configured to radiate light beams into the iris of the user via the arranged lenses by emitting the light beams toward the arranged lenses, and a controller configured to change positions of the arranged lenses based on a distance between the device and the iris, in which the lens array is positioned between the light source and the iris.

The device may further include a camera configured to capture the iris of the user in which the controller may be further configured to use an image of the iris to calculate the distance between the device and the iris.

The controller may be further configured to adjust an interval between the arranged lenses according to the distance between the device and the iris.

The controller may be further configured to focus the light beams emitted from the light source by decreasing the interval between the arranged lenses.

The controller may be further configured to calculate the distance between the device and the iris based on a direction perpendicular to the device.

The controller may be further configured to set a quantity of first light beams to be radiated toward a lens corresponding to a central region of the iris to be less than a quantity of second light beams to be radiated toward a lens corresponding to a peripheral region of the iris.

The controller may be further configured to sense movement of the iris and move the arranged lenses based on the movement of the iris.

The controller may be further configured to determine a moving direction and a moving distance of the iris based on a direction horizontal to the device and may move the arranged lenses the same distance in the same direction based on the determined moving direction and moving distance.

The controller may change the positions of the arranged lenses by applying a voltage to electrodes arranged in the lens array.

The light beams that are emitted from the light source and transmitted through the arranged lenses overlap one another, and the overlapped light beams include a quantity within a predetermined range and are radiated to an entire area of the iris.

In accordance with another aspect of the present disclosure, a method of radiating light from a device to capture an iris of a user is provided. The method includes determining a distance between the device and the iris, changing positions of arranged lenses forming a lens array based on the determined distance, emitting light beams toward the arranged lenses, in which the lens array is positioned between a light source and the iris, and the emitted light beams reach the iris of the user via the arranged lenses.

The method may further include capturing an image of the iris of the user, in which the determining of the distance comprises using the captured image of the iris to calculate the distance between the device and the iris.

The changing of the positions of the arranged lenses may include adjusting an interval between the arranged lenses according to the distance between the device and the iris.

The changing of the positions of the arranged lenses may include decreasing an interval between the arranged lenses wherein the light beams emitted from the light sources are transmitted through the arranged lenses having the decreased interval and thus focused.

The determining of the distance between the device and the iris may include calculating the distance between the device and the iris based on a direction perpendicular to the device.

The method may further include setting a quantity of the light beams to be radiated toward the lenses, in which a quantity of first light beams to be radiated toward a lens corresponding to a central region of the iris is set to be less than a quantity of second light beams to be radiated toward a lens corresponding to a peripheral region of the iris.

The changing of the positions may include sensing movement of the iris and moving the arranged lenses based on the movement of the iris.

The changing of the positions of the arranged lenses may include determining a moving direction and a moving distance of the iris based on a direction horizontal to the device and moving the arranged lenses the same distance in the same direction based on the determined moving direction and moving distance.

The changing of the positions of the arranged lenses may include changing the positions of the arranged lenses forming the lens array by applying a voltage to electrodes arranged in the lens array.

In accordance with another aspect of the present disclosure, a non-transitory computer-readable recording medium stores a computer program for executing the above method is provided.

Other aspects, advantages, and salient features of the disclosure will become apparent to those skilled in the art from the following detailed description, which, taken in conjunction with the annexed drawings, discloses various embodiments of the present disclosure.

BRIEF DESCRIPTION OF THE DRAWINGS

The above and other aspects, features, and advantages of certain embodiments of the present disclosure will be more apparent from the following description taken in conjunction with the accompanying drawings, in which.

Throughout the drawings, like reference numerals will be understood to refer to like parts, components, and structures.

DETAILED DESCRIPTION

The following description with reference to the accompanying drawings is provided to assist in a comprehensive understanding of various embodiments of the present disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the present disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the present disclosure. Accordingly, it should be apparent to those skilled in the art that the following description of various embodiments of the present disclosure is provided for illustration purpose only and not for the purpose of limiting the present disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

In this disclosure, when one part (or element, device, etc.) is referred to as being "connected" to another part (or element, device, etc.), it should be understood that the former can be "directly connected" to the latter, or "electrically connected" to the latter via an intervening part (or element, device, etc.). Furthermore, when one part is referred to as "comprising (or including or having)" other elements, it should be understood that it can comprise (or include or have) only those elements, or other elements as well as those elements unless specifically described otherwise.

As used herein, the term "and/or" includes any and all combinations of one or more of the associated listed items.

Expressions such as "at least one of," when preceding a list of elements, modify the entire list of elements and do not modify the individual elements of the list.

Hereinafter, various embodiments of the present disclosure will be described in detail with reference to the accompanying drawings.

Figure 1:
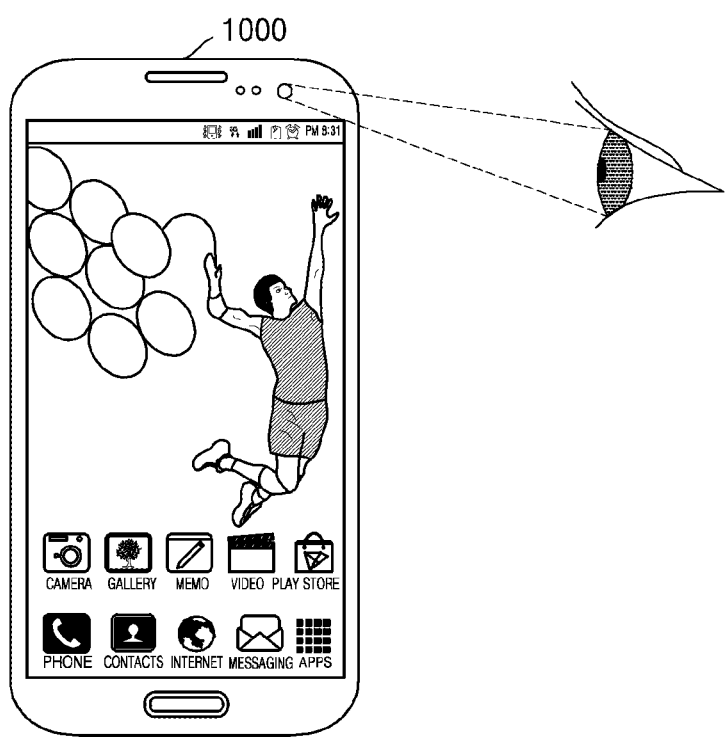
FIG. 1 is a diagram of a device to capture an iris of a user according to various embodiments of the present disclosure.

FIG. 1 is a diagram of a device to capture an iris of a user according to various embodiments of the present disclosure.

Referring to FIG. 1, a device 1000 may measure a position of an iris of a user or a distance to the iris and radiate light into the iris in order to capture the iris. The device 1000 may adjust the quantity of light radiated into the iris in a relatively uniform manner and may adjust a direction of the radiated light by moving a lens in the device 1000 as the iris is moved.

In addition, the iris captured by the device 1000 may be used to authenticate a user of the device 1000 to provide a predetermined service. The service includes any service provided by service providers or device 1000. Examples of the service may include a broadcasting service, a content sharing service, a content providing service, a power management service, a game providing service, a chatting service, a word processing service, a search service, a call service, a photograph capturing service, a transportation recommendation service, and a video playback service. However, embodiments of the present disclosure are not limited thereto.

The device may include, but is not limited to, a smartphone, a tablet personal computer (PC), a smart TV, a cell phone, a personal digital assistant (PDA), a laptop, a media player, a micro server, a global positioning system (GPS) device, an e-book terminal, a digital broadcasting terminal, a navigation device, a kiosk, a Moving Picture Experts Group phase 1 or phase 2 (MPEG-1 or MPEG-2) audio layer 3 (MP3) player, a digital camera, and other mobile or non-mobile computing devices. In addition, the device 1000 may be a wearable device, such as a wrist watch, eyeglasses, a hair band, and a ring, which includes a communication function and a data processing function. However, embodiments of the present disclosure are not limited thereto, and the device 1000 may include any equipment that may radiate light into an iris of a user.

Figure 2:
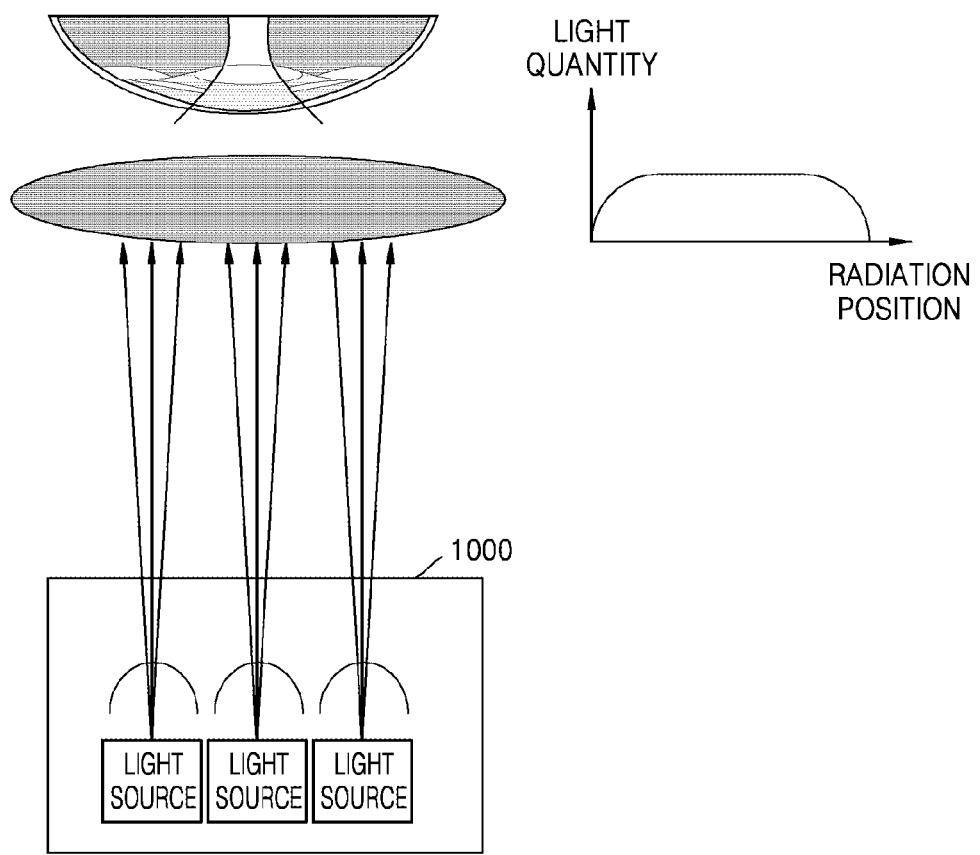
FIG. 2 is a diagram of a device that radiates light to lenses included in a lens array according to various embodiments of the present disclosure.

FIG. 2 is a diagram of a device that radiates light to lenses included in a lens array according to various embodiments of the present disclosure.

Referring to FIG. 2, the device 1000 may radiate light emitted from a plurality of light sources into the iris of the user using a lens array in which a plurality of lenses are arranged. The light radiated from the plurality of light sources may partially overlap one another, and thus the device 1000 may radiate a predetermined quantity of light into the iris of the user. The device 1000 may radiate light having a relatively uniform quantity of light.

Figure 3:
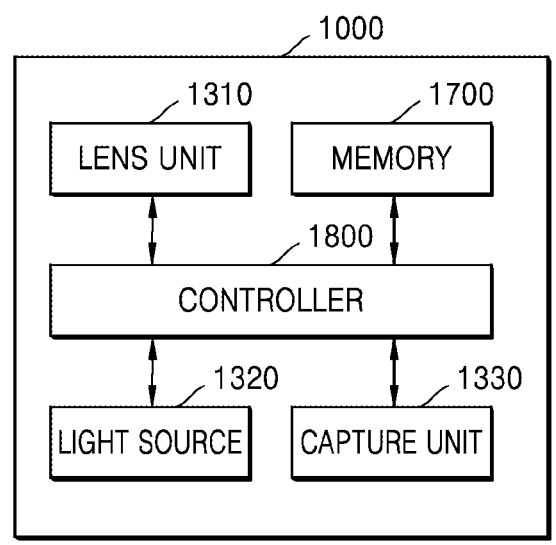
FIGS. 3 and 4 are block diagrams of a device that captures an image of an iris of a user according to various embodiments of the present disclosure.
Figure 4:
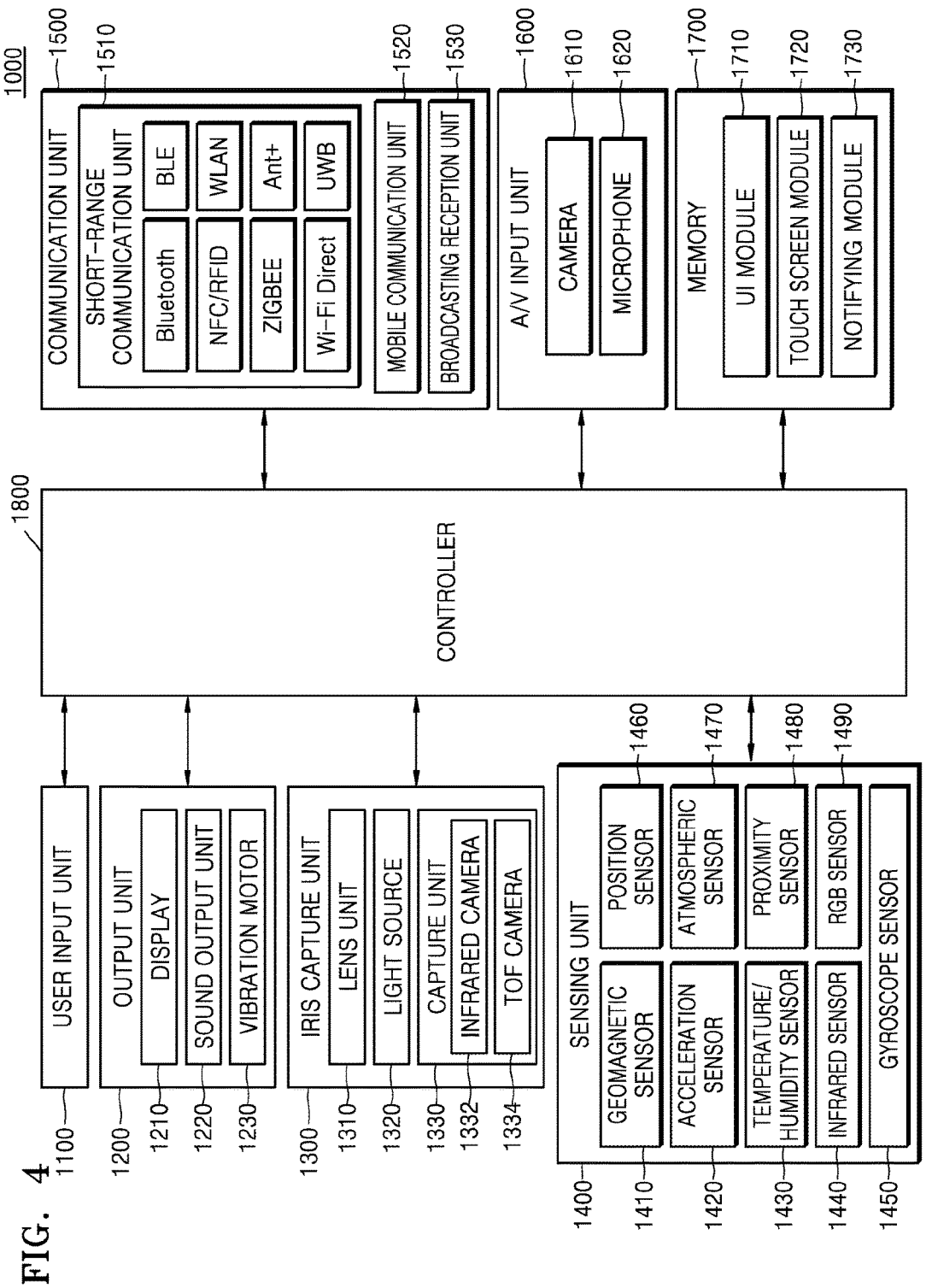

FIGS. 3 and 4 are block diagrams of a device that captures an image of an iris of a user according to various embodiments of the present disclosure.

Referring to FIG. 3, the device 1000 may include a lens unit 1310, a light source 1320, a capture unit 1330, a memory 1700, and a controller 1800. However, not all of the elements shown in FIG. 3 are essential to the device 1000. The device 1000 may be implemented with more elements than those shown in FIG. 3 or may be implemented with fewer elements than those shown in FIG. 3.

Referring to FIG. 4, the device 1000 may further include a user input unit 1100, an output unit 1200, an iris capture unit 1300, a sensing unit 1400, a communication unit 1500, and an audio/video (A/V) input unit 1600. The iris capture unit 1300 may include a lens unit 1310, a light source 1320, a capture unit 1330, and the capture unit 1330 may include an infrared camera 1332 and a time-of-flight (TOF) camera 1334.

The user input unit 1100 includes a user input device for receiving user input for controlling the device 1000. For example, examples of the user input unit 1100 may include, but are not limited to, a key pad, a dome switch, a touch pad (a contact capacitance type, a pressure resistance type, an infrared sensing type, a surface ultrasonic wave conduction type, an integral tension measurement type, a piezoelectric effect type, etc.), a jog wheel, a jog switch, etc.

The user input unit 1100 may receive a user input for capturing the iris of the user. In addition, the user input unit 1100 may receive a user input for using a predetermined service.

The output unit 1200 may output an audio signal, a video signal, and/or a vibration signal. The output unit 1200 may include a display 1210, a sound output unit 1220, and a vibration motor 1230.

The display 1210 outputs information processed in the device 1000. For example, the display 1210 may display a user interface for capturing the iris of the user. In addition, the display 1210 may display a user interface for using a predetermined service.

When the display 1210 and a touch pad form a layered structure and are implemented as a touch screen, the display 1210 may be used as an input device in addition to an output device. The display 1210 may include at least one of a liquid crystal display (LCD), a thin film transistor-LCD (TFT-LCD), an organic light emitting diode (OLED) display, a flexible display, a three-dimensional (3D) display, and an electrophoretic display. The device 1000 may include two or more displays 1210 according to the implementation of the device 1000. In this case, the two or more displays 1210 may be disposed to face each other using a hinge.

The sound output unit 1220 outputs audio data received from the communication unit 1500 or stored in the memory 1700. The sound output unit 1220 may output an acoustic signal related to a function (e.g., a call signal reception sound, a message reception sound, or an alarm sound) performed by the device 1000. The sound output unit 1220 may include a speaker, a buzzer, etc.

The vibration motor 1230 may output a vibration signal. For example, the vibration motor 1230 may output a vibration signal corresponding to output of audio data or video data (e.g., a call signal reception sound, a message reception sound, etc.) In addition, the vibration motor 1230 may output the vibration signal when a touch is input to the touch screen.

The iris capture unit 1300 may be controlled by the controller 1800 to capture the iris of the user. The iris capture unit 1300 may include the lens unit 1310, the light source 1320, and the capture unit 1330.

The lens unit 1310 may include a plurality of lenses that are arranged. The lens array may be formed by arranging the plurality of lenses in either one dimension or two dimensions. For example, the plurality of lenses may be arranged in a row or arranged on a predetermined surface. In addition, the lens unit 1310 may be controlled by the controller 1800 to move the lenses or change refractive indices of the lenses. For example, each of the lenses forming the lens array may include a membrane lens, an electrowetting lens, and a liquid crystal lens.

The membrane lens may have a thin film with curvature changed with a change in pressure applied to the film of the lens. As the curvature of the thin film is changed, the curvature of the lens may be changed. The pressure applied to the thin film of the lens may be applied by a fluid (e.g., water, oil, etc.) or air inside the lens. The membrane lens may include, for example, an actuator type membrane lens and a micro fluid pump type lens.

The electrowetting lens may be adjusted by changing the shape of a boundary surface between two fluids. The fluids forming the electrowetting lens may be conductive. Surface tensions of the fluids may be controlled by applying a predetermined voltage to the fluids forming the electrowetting lens. Thus, the curvature of the boundary surface between the two fluids forming the electrowetting lens may be changed, and a refractive index of the electrowetting lens may be adjusted.

The liquid crystal lens may adjust its refractive index using characteristics of materials in the liquid crystal lens. Positions and directions of the materials inside the liquid crystal lens may be adjusted by applying a voltage to the materials in the liquid crystal lens. Thus, a refractive index of the liquid crystal lens may be adjusted.

The light source 1320 may be controlled by the controller 1800 to radiate light into an iris of a user. The light source 1320 may radiate light to a plurality of lenses included in a lens array and radiate the light into the iris of the user via the plurality of lenses. The light source 1320 may radiate light having different light intensities depending on the positions of the lenses. The light radiated from the light source 1320 may include, for example, infrared light and natural light. However, embodiments of the present disclosure are not limited thereto.

The capture unit 1330 may be controlled by the controller 1800 to capture the iris of the user. The capture unit 1330 may include, for example, the infrared camera 1332 and the TOF camera 1334.

The sensing unit 1400 may sense a state of the device 1000 or a state surrounding the device 1000 and may deliver the sensed information to the controller 1800.

The sensing unit 1400 may include, but is not limited to, at least one of a magnetic sensor 1410, an acceleration sensor 1420, a temperature/humidity sensor 1430, an infrared sensor 1440, a gyroscope sensor 1450, a positioning sensor 1460 (e.g., a GPS sensor), an air pressure sensor 1470, a proximity sensor 1480, and an red, green, and blue (RGB) sensor (e.g., an illumination sensor) 1490. A function for each sensor may recognized by those skilled in the art, and thus its detailed description will be omitted.

The communication unit 1500 may include one or more elements for communicating with another device (not shown) and a server (not shown). For example, the communication unit 1500 may include a short-range wireless communication unit 1510, a mobile communication unit 1520, and a broadcast receiving unit 1530.

The short-range wireless communication unit 1510 may include, but is not limited to, a Bluetooth® communication unit, a Bluetooth low energy (BLE) communication unit, a near field communication unit, a wireless LAN (WLAN) communication unit, a Zigbee® communication unit, an infrared data association (IrDA) communication unit (not shown), a wireless fidelity (Wi-Fi) Direct (WFD) communication unit, a ultra wide band (UWB) communication unit, and an Ant+ communication unit.

The mobile communication unit 1520 transmits and receives a radio signal to and from at least one of a base station, an external terminal, and a server on a mobile communication network. The radio signal may include a voice call signal, a video call signal, or various forms of data according to transmission and/or reception of a text and/or multimedia message.

The broadcast receiving unit 1530 receives a broadcast signal and/or broadcast-related information over a broadcast channel. The broadcast channel may include a satellite channel and a terrestrial channel. Depending on the implementation, the device 1000 may not include the broadcast receiving unit 1530.

In addition, the communication unit 1500 may receive a predetermined service and may transmit and/or receive information needed to authenticate a user who will use the service to and/or from another device (not shown) and a server (not shown).

The A/V input unit 1600 may include a camera 1610 and a microphone 1620. The camera 1610 may obtain a frame of a still image or moving image through an image sensor in a video call mode or a capture mode. The image captured through the camera 1610 may be processed by the controller 1800 or by a separate image processing unit (not shown).

The image frame processed by the camera 1610 may be stored in the memory 1700 or transmitted through the communication unit 1500. Two or more cameras 1610 may be provided according to an aspect of the configuration of the terminal. The camera 1610 may be included in the above-described capture unit 1330 or may be implemented as an element separate from the capture unit 1330.

The microphone 1620 receives and processes an external acoustic signal into electrical voice data. For example, the microphone 1620 may receive an acoustic signal from an external device or a speaker. The microphone 1620 may use various noise removal algorithms for removing noise generated while receiving the external acoustic signal.

The memory 1700 may store a program for processing and controlling the controller 1800 and may also store data that is input to the device 1000 and output from the device 1000.

The memory 1700 may include a flash memory type, hard disk type, multimedia card micro type, or card type memory (e.g., a secure digital (SD) or extreme digital (XD) memory), or at least one type of storage medium among a random access memory (RAM), a static random access memory (SRAM), a read-only memory (ROM), an electrically erasable programmable read-only memory (EEPROM), a programmable read-only memory (PROM), a magnetic memory, a magnetic disk, and an optical disc.

Programs stored in the memory 1700 may be classified into a plurality of modules according to the functions of the programs and, for example, may be classified into a user interface (UI) module 1710, a touch screen module 1720, an alarm module 1730, and so on.

The UI module 1710 may provide a specialized UI, a graphical user interface (GUI), or the like, for each application. The touch screen module 1720 may sense a touch gesture of a user on a touch screen (e.g., display 1210) and deliver information regarding the touch gesture to the controller 1800. The touch screen module 1720 according to some embodiments of the present disclosure may recognize and analyze a touch code. The touch screen module 1720 may be configured as separate hardware including a controller.

In order to sense a touch or a proximity touch on the touch screen, various sensors may be provided inside or near the touch screen. An example of the sensor for sensing the touch on the touch screen is a tactile sensor. The tactile sensor senses a touch by a specific object to a degree that a human can feel or more. The tactile sensor may sense various information such as a roughness of a touched surface, a stiffness of a touched object, a temperature of a touched point, etc.

Moreover, an example of the sensor for sensing the touch on the touch screen is a proximity sensor.

The proximity sensor uses an electromagnetic force or infrared light to detect an object approaching a detection surface or an object near the detection surface without any mechanical contact. Examples of the proximity sensor include a transmissive photoelectric sensor, a direct reflective photoelectric sensor, a mirror reflective photoelectric sensor, a high-frequency oscillation proximity sensor, a capacitive proximity sensor, a magnetic proximity sensor, and an infrared proximity sensor. Examples of the touch gesture of the user may include a tap, a touch and hold, a double tap, a drag, panning, a flick, a drag and drop, and a swipe.

The alarm module 1730 may generate a signal for informing of the occurrence of an event in the device 1000. Examples of the event occurring in the device 1000 may include reception of a call signal, reception of a message, input of a key signal, and a scheduled event. The alarm module 1730 may output an alarm signal in the form of a video signal through the display 1210, output an alarm signal in the form of an audio signal through the sound output unit 1220, and output an alarm signal in the form of a vibration signal through the vibration motor 1230.

The controller 1800 controls an overall operation of the device 1000. For example, the controller 1800 may control overall operations of the user input unit 1100, the output unit 1200, the sensing unit 1400, the communication unit 1500, the A/V input unit 1600, the memory 1700, and the iris capture unit 1300 by executing programs stored in the memory 1700.

The controller 1800 may detect a position of an iris of the user. The controller 1800 may capture an image of the iris of the user using a camera included in the device 1000 and detect a position of the iris on the basis of the captured image. In addition, the controller 1800 may calculate a distance from the device 1000 to the iris on the basis of the captured image. In this case, the controller 1800 may calculate a relative distance (i.e., a distance index) between the device 1000 and the iris of the user on the basis of a pupil of the user included in the captured image. The controller 1800 may detect the pupil from the captured iris image and calculate a distance from the device 1000 to the iris from the size of the detected pupil. When the size of the detected pupil is larger, the controller 1800 may determine that the distance from the device 1000 to the iris of the user is smaller. When the size of the detected pupil is smaller, the controller 1800 may determine that the distance from the device 1000 to the iris of the user is larger. The controller 1800 may calculate the distance from the device 1000 to the iris according to a predetermined criterion on the basis of the size of the detected pupil.

In addition, the controller 1800 may determine the distance from the device 1000 to the iris of the user using the TOF camera 1334. The controller 1800 may radiate light into the iris of the user and receive light reflected from the iris of the user. For example, the controller 1800 may control the TOF camera 1334 to radiate light emitted from a light source of the TOF camera 1334 into the iris of the user and receive light reflected from the iris. In this case, a light source of the TOF camera 1334 may be included in the light source 1320 or may be separated from the light source 1320. In addition, the controller 1800 may use a phase difference between the radiated light and the reflected light to calculate the distance between the device 1000 and the iris of the user.

However, the method of measuring the distance between the device 1000 and the iris of the user is not limited thereto. For example, the controller 1800 may use various sensors, such as an infrared sensor and an ultrasonic sensor, to measure the distance between the device 1000 and the iris of the user.

In addition, the controller 1800 may determine a relative position and direction of the iris with respect to the device 1000 on the basis of the captured image. The controller 1800 may determine the relative position and direction of the pupil with respect to the device 1000 on the basis of the position of the pupil in the captured image. The controller 1800 may detect the position of the pupil at predetermined periods. In addition, the controller 1800 may detect the position of the pupil when a predetermined event occurs.

The controller 1800 may determine positions of lenses in a lens array. The controller 1800 may determine the positions of the lenses in the lens array on the basis of the distance between the device 1000 and the iris. As the distance between the device 1000 and the iris becomes larger, the controller 1800 may reduce the interval between the lenses in the lens array. The device 1000 may determine the positions of the lenses in consideration of the quantity of light to be radiated to the lenses.

In addition, the controller 1800 may determine the positions of the lenses in the lens array to uniformly move the lenses on the basis of the relative position of the iris with respect to the device 1000. For example, as described below with respect to FIG. 11, the controller 1800 may determine the positions of the lenses in the lens array to move the lenses the same distance in the same direction.

In addition, a criterion for determining the positions of the lenses may be predetermined and may be set in consideration of, for example, the distance between the device 1000 and the iris, the relative position of the iris with respect to the device 1000, the intensity of light radiated to the lenses, and refractive indices of the lenses. In addition, the light that has passed through the lenses is combined and then reaches the iris, and the criterion for determining the positions of the lenses may be determined such that the quantity of the combined light that has reached the iris has a predetermined value over the entire area of the iris.

The controller 1800 may determine the quantity of light to be radiated to the lenses in the lens array. The controller 1800 may determine the quantity of light to be radiated to the lenses in the lens array on the basis of the position of the iris. In addition, the controller 1800 may determine the quantity of light to be radiated to the lenses in the lens array on the basis of the calculated distance. As the distance between the device 1000 and the iris becomes larger, the controller may increase the quantity of light to be radiated to the lens.

In addition, the controller 1800 may determine the quantity of light to be different for each lens in the lens array. For example, the controller 1800 may set the quantity of light to be radiated to a lens corresponding to a central region of the iris to be smaller and may set the quantity of light to be radiated to a lens corresponding to a region further from the central region to be larger.

In addition, a criterion for determining the quantity of light to be radiated to the lenses may be predetermined and may be set in consideration of, for example, the distance between the device 1000 and the iris, the relative position of the iris with respect to the device 1000, positions of the lenses with respect to the light source and the iris, and refractive indices of the lenses. In addition, the light passing through the lenses is combined and then reaches the iris, and the criterion for determining the quantity of light to be radiated to the lenses may be determined such that the quantity of the combined light that has reached the iris has a predetermined value over the entire area of the iris.

The controller 1800 may adjust positions of the lenses in the lens array according to the determined positions. The controller 1800 may move the lenses in the lens array according to the determined positions.

A plurality of electrodes may be positioned in the lens array, and the controller 1800 may apply a voltage to some of the electrodes to move the lenses. The lenses may be moved to regions including points at which the electrodes to which the voltage is applied are positioned. Alternatively, the controller 1800 may move the lenses by moving a plate in which the lens array is formed. However, embodiments of the present disclosure are not limited thereto.

The controller 1800 may radiate light into the lenses according to the determined quantity of light. The controller 1800 may use a plurality of light sources to radiate light to the lenses. Alternatively, the controller 1800 may use a plane lens including a plurality of triangular pin lenses to disperse light radiated from a light source and radiate the dispersed light into the lenses. However, embodiments of the present disclosure are not limited thereto.

In addition, the controller 1800 may sense a change in position of the iris in real time and adjust the positions of the lenses in the lens array and the quantities of the light radiated to the lenses according to the changed position of the iris.

FIGS. 5A, 5B, 5C, and 5D are diagrams of a lens array according to various embodiments of the present disclosure.

Figure 5A:
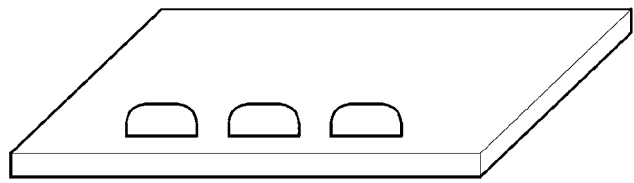
FIGS. 5A, 5B, 5C and 5D are diagrams of an example of a lens array according to various embodiments of the present disclosure.

Referring to FIG. 5A, the lens array may include lenses arranged in one dimension. The plurality of lenses may be arranged in a row along a predetermined line.

Figure 5B:
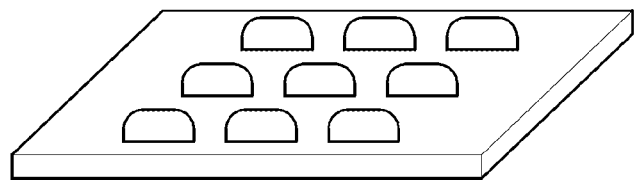

Referring to FIG. 5B, the lens array may include lenses arranged in two dimensions. The plurality of lenses may be arranged at intervals on a predetermined surface.

Figure 5C:
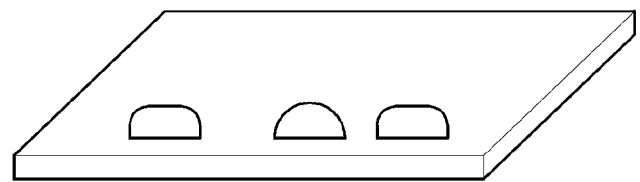

Referring to FIG. 5C, the lenses may be arranged in one dimension and at different intervals. In addition, the lenses may have different refractive indices. In addition, the lenses may have different sizes. The intervals between, the refractive indices of, and the sizes of the lenses constituting the lens array may be predetermined. The intervals between, the refractive indices of, and the sizes of the lenses constituting the lens array may be changed in real time.

Figure 5D:
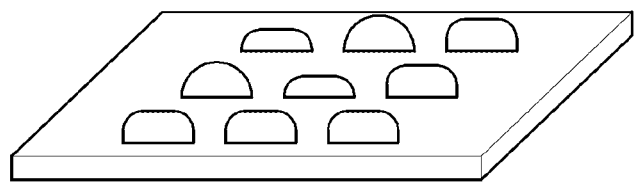

Referring to FIG. 5D, the lenses may be arranged in two dimensions and at different intervals. In addition, the lenses may have different refractive indices. In addition, the lenses may have different sizes. The intervals between, the refractive indices of, and the sizes of the lenses may be predetermined. The intervals between, the refractive indices of, and the sizes of the lenses may be changed in real time depending on the situation.

The lens array may include a reflective plate. For example, the reflective plate may be on a rear surface of each of the lenses, and a portion of light radiated to the lens may be reflected by the reflective plate and then transmitted through the lens. The light reflected by the reflective plate may be refracted by the lens and then radiated into the iris.

In addition, a plate constituting the lens array of FIGS. 5A to 5D may be made of a flexible material, and the device may bend the plate to adjust the positions and directions of the lenses.

FIGS. 6A, 6B, 6C and 6D are diagrams of an example in which a device radiates light in a quantity within a predetermined range into an iris of a user according to various embodiments of the present disclosure.

Figure 6A:
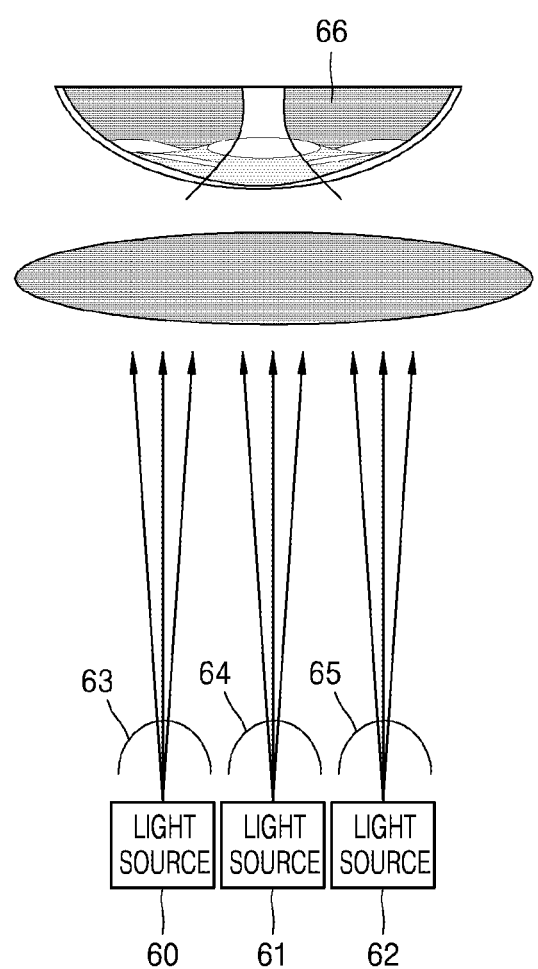
FIGS. 6A, 6B, 6C and 6D are diagrams of an example in which a device radiates light in a quantity within a predetermined range into an iris of a user according to various embodiments of the present disclosure.

Referring to FIG. 6A, according to some embodiments of the present disclosure, a light source 60 may radiate light into an iris 66 of a user via a lens 63 in a lens array, a light source 61 may radiate light into the iris 66 of the user via a lens 64 in the lens array, and a light source 62 may radiate light into the iris 66 of the user via a lens 65 in the lens array.

Figure 6B:
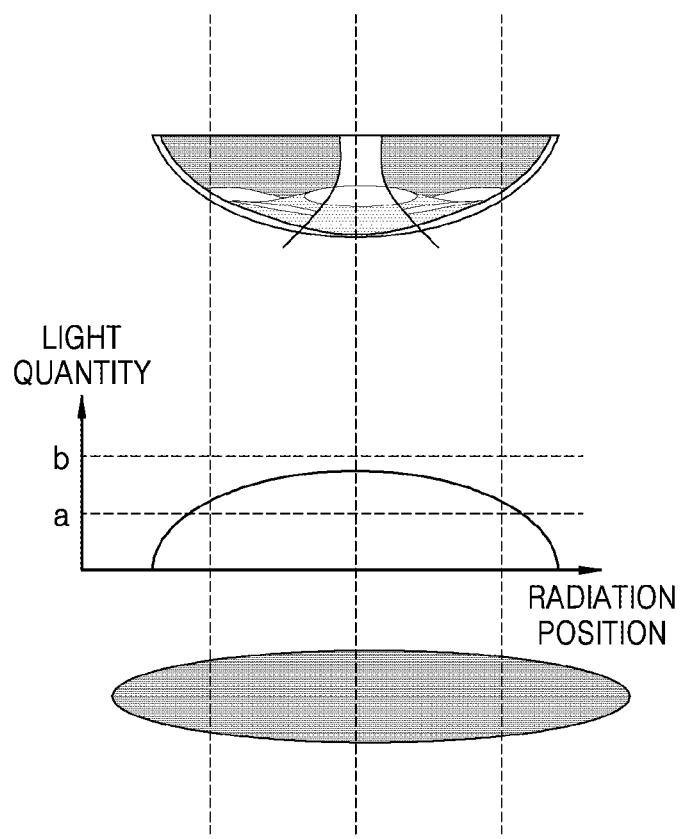

Referring to FIG. 6B, at least some of the light radiated from the light source 60, the light radiated from the light source 61, and the light radiated from the light source 62 may overlap one another. Thus, light in a relatively uniform quantity ranging from light quantity a to light quantity b may be radiated into the iris, and the user may feel less glare when his/her iris is captured.

Figure 6C:
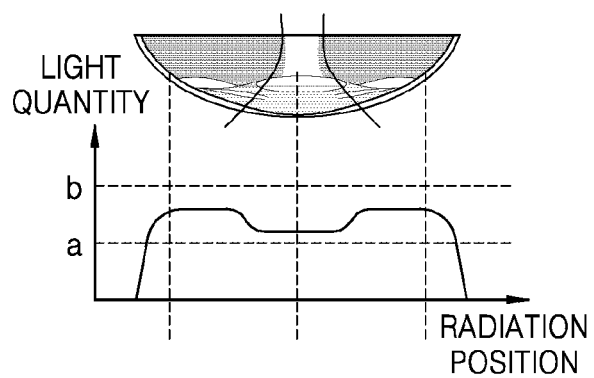

Referring to FIG. 6C, as a slope from a light quantity 0 to light quantity a is a curved line that indicates the radiated light quantity, at least some of the light radiated from the light source 60, the light radiated from the light source 61, and the light radiated from the light source 62 may overlap one another. A relatively smaller quantity of light may be radiated to a pupil portion.

Figure 6D:
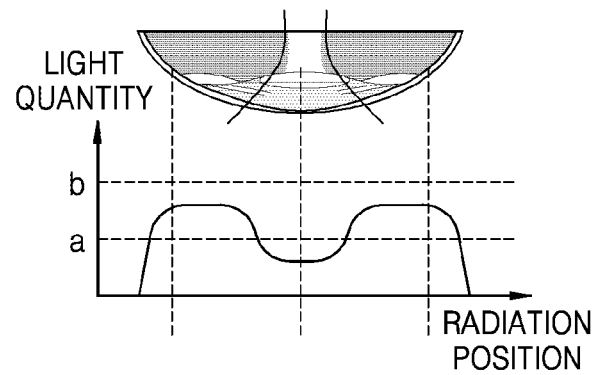

Referring to FIG. 6D, at least some of the light radiated from the light source 60, the light radiated from the light source 61, and the light radiated from the light source 62 may overlap one another such that a quantity of light radiated to the pupil portion of the user is less than light quantity a.

Figure 7A:
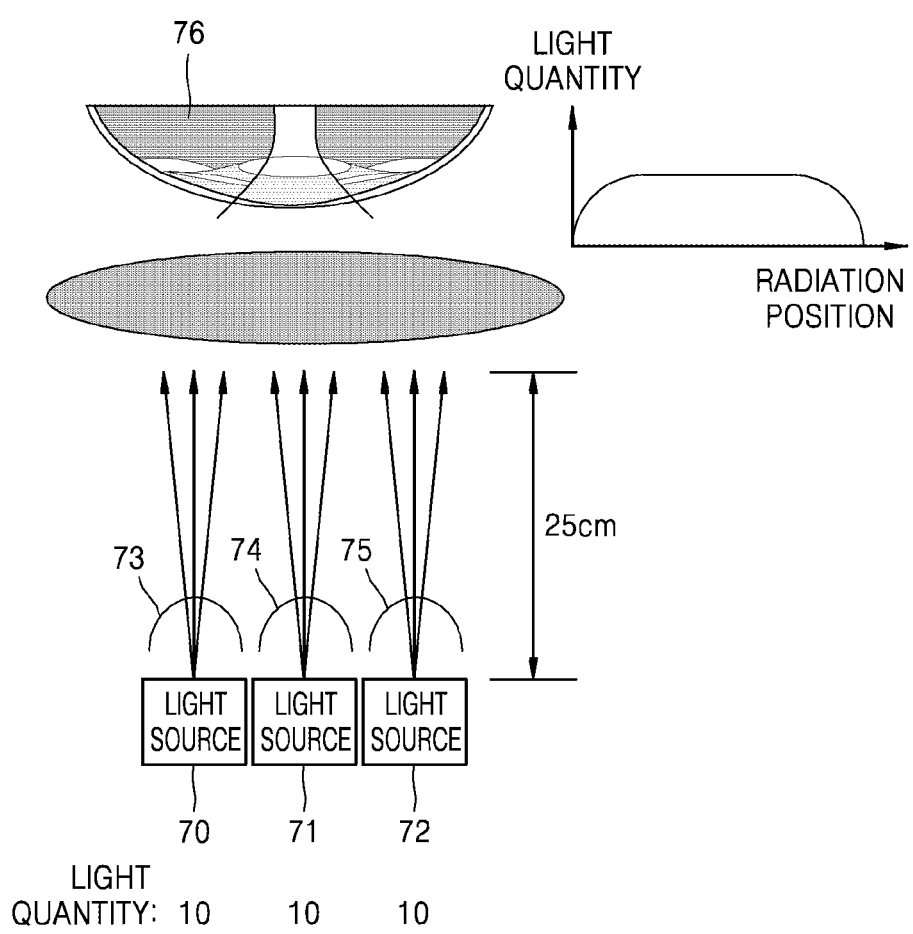
FIGS. 7A and 7B are diagrams of an example in which a device that adjusts the quantity of light radiated from a light source according to various embodiments of the present disclosure.
Figure 7B:
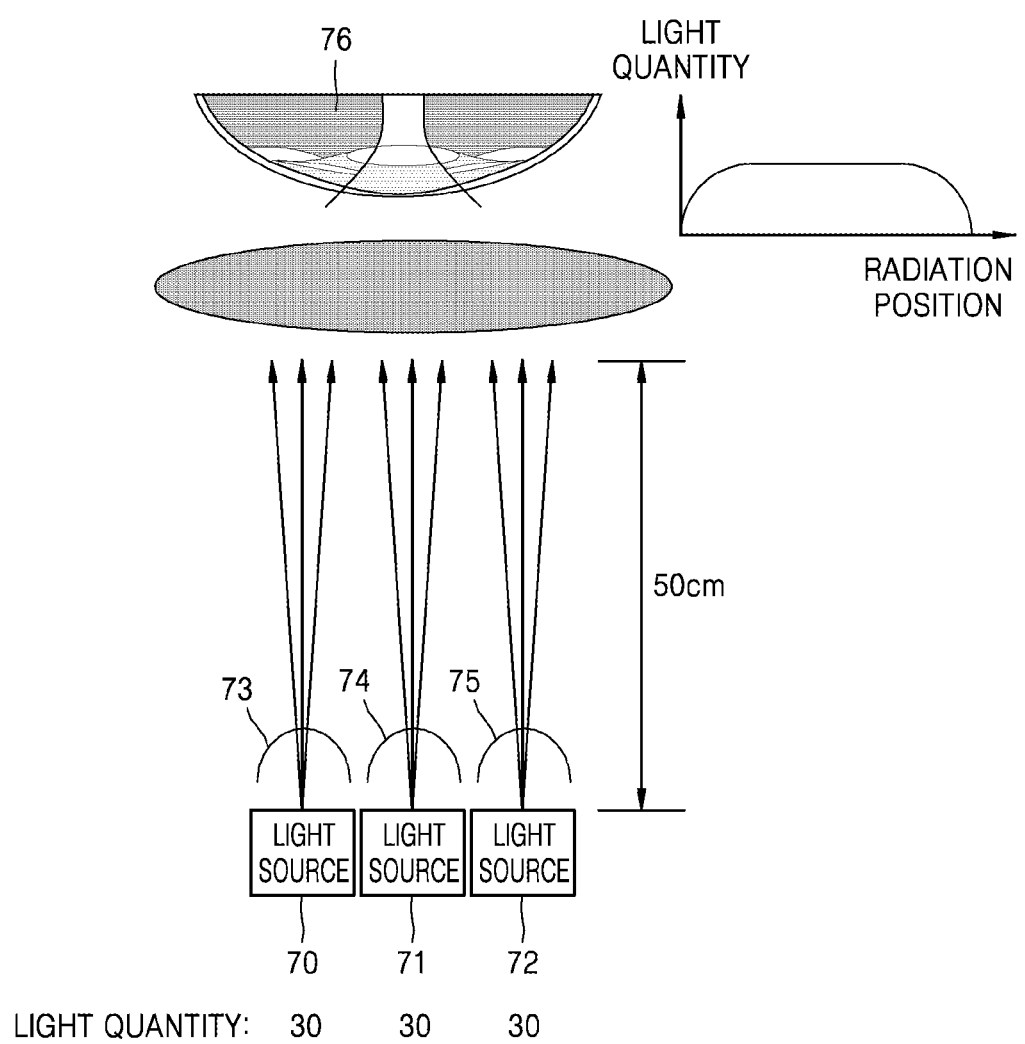

FIGS. 7A and 7B are diagrams of an example in which a device adjusts a quantity of light radiated from a light source according to various embodiments of the present disclosure.

Referring to FIG. 7A, when a distance from a light source 70, 71, or 72 to an iris 76 is 25 cm, the light source 70 may radiate light in a quantity of 10, the light source 71 may radiate the light in a quantity of 10, and the light source 73 may radiate the light in a quantity of 10.

Referring to FIG. 7B, when the distance from the light source 70, 71, or 72 to the iris 76 increases to 50 cm, the light source 70 may radiate light in a quantity of 30, the light source 71 may radiate the light in a quantity of 30, and the light source 73 may radiate the light in a quantity of 30. In this case, a variation of the light quantity radiated from the light source 70, 71, or 72 may be predetermined according to a change in distance from the light source 70, 71, or 72 into the iris 76.

Figure 8:
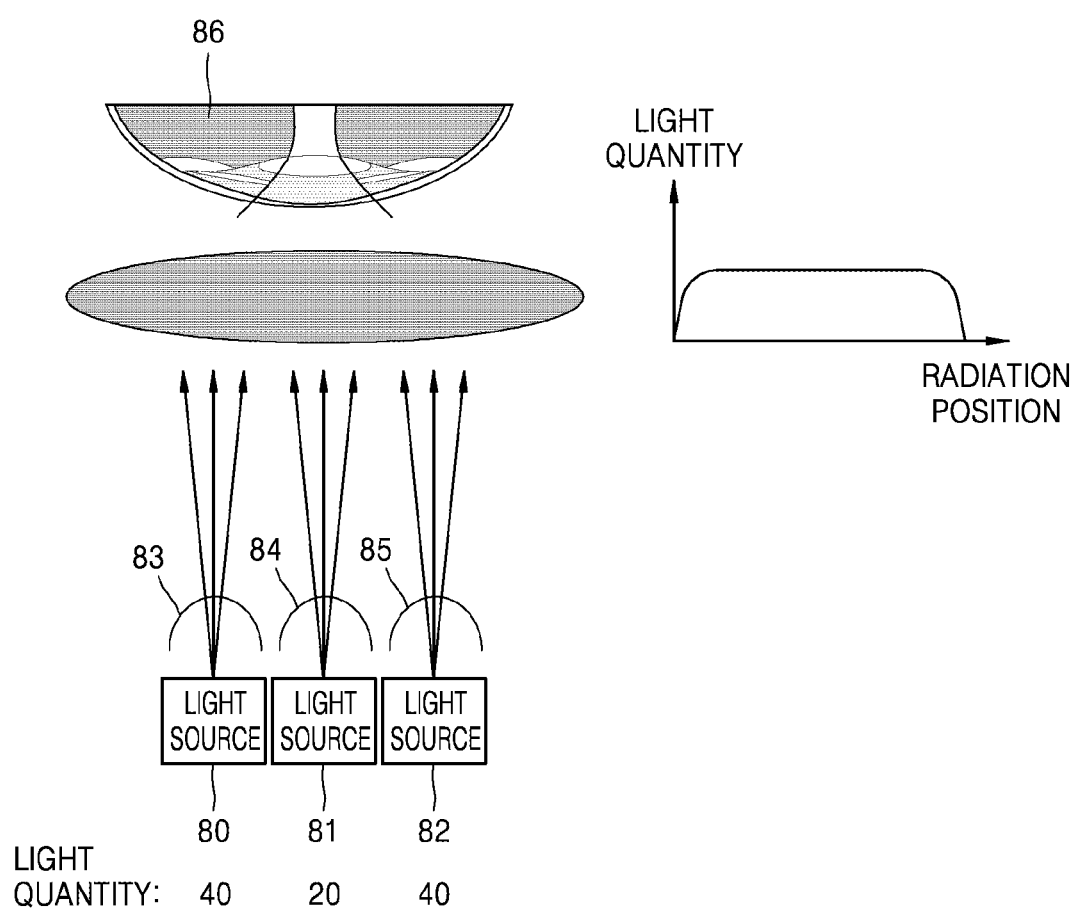
FIG. 8 is a diagram of an example in which a device adjusts a quantity of light radiated to lenses included in a lens array according to various embodiments of the present disclosure.

FIG. 8 is a diagram of an example in which a device adjusts a quantity of light radiated to lenses included in a lens array according to various embodiments of the present disclosure.

Referring to FIG. 8, the device may set the quantity of light radiated from a light source 81 closest to a central region of an iris to be smaller than the quantity of light to be radiated from the light source 80 and the quantity of light to be radiated from the light source 82. Thus, the light source 81 may radiate light in a quantity of 20 through a lens 84. In addition, the light source 80 may radiate light in a quantity of 40 through a lens 83, and the light source 82 may radiate light in a quantity of 40 through a lens 85.

Figure 9:
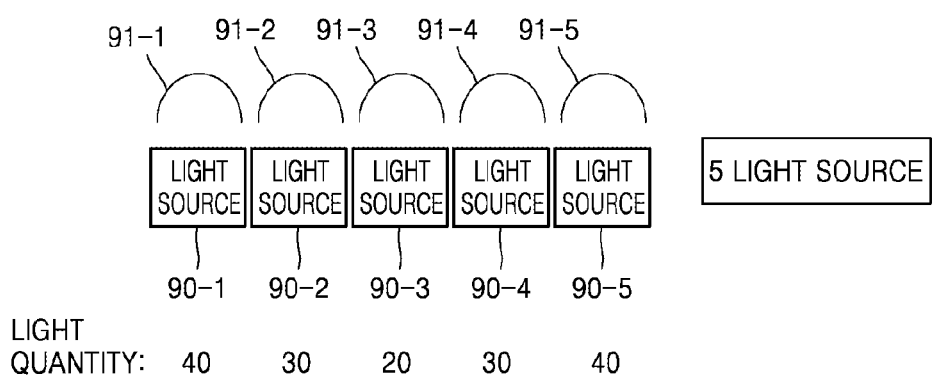
FIG. 9 is a diagram illustrating examples of a lens array and a light source according to various embodiments of the present disclosure.

FIG. 9 is a diagram illustrating examples of a lens array and a light source according to various embodiments of the present disclosure.

Referring to FIG. 9, the device may radiate light into an iris using five light sources 90-1, 90-2, 90-3, 90-4, and 90-5. The five light sources 90-1, 90-2, 90-3, 90-4, and 90-5 may correspond to five lenses 91-1, 91-2, 91-3, 91-4, and 91-5 included in the lens array. In addition, to radiate light in a quantity within a predetermined range, the device may set the quantity of light radiated from a light source corresponding to a region further from the central region of the iris to be larger than the quantity of light radiated from a light source corresponding to a region closer to the central region of the iris. For example, the light source 90-3 may radiate light in a quantity of 20, the light source 90-2 and the light source 90-4 may radiate light in a quantity of 30, and the light source 90-1 and the light source 90-5 may radiate light in a quantity of 40. Thus, a relatively uniform quantity of light may be radiated into the iris of the user.

However, embodiments of the present disclosure are not limited thereto, and the number of light sources and the quantities of light radiated from the light sources may be set to various values. For example, light may be radiated from one light source to a plurality of lenses, and may be changed variously according to a predetermined criterion.

Figure 10:
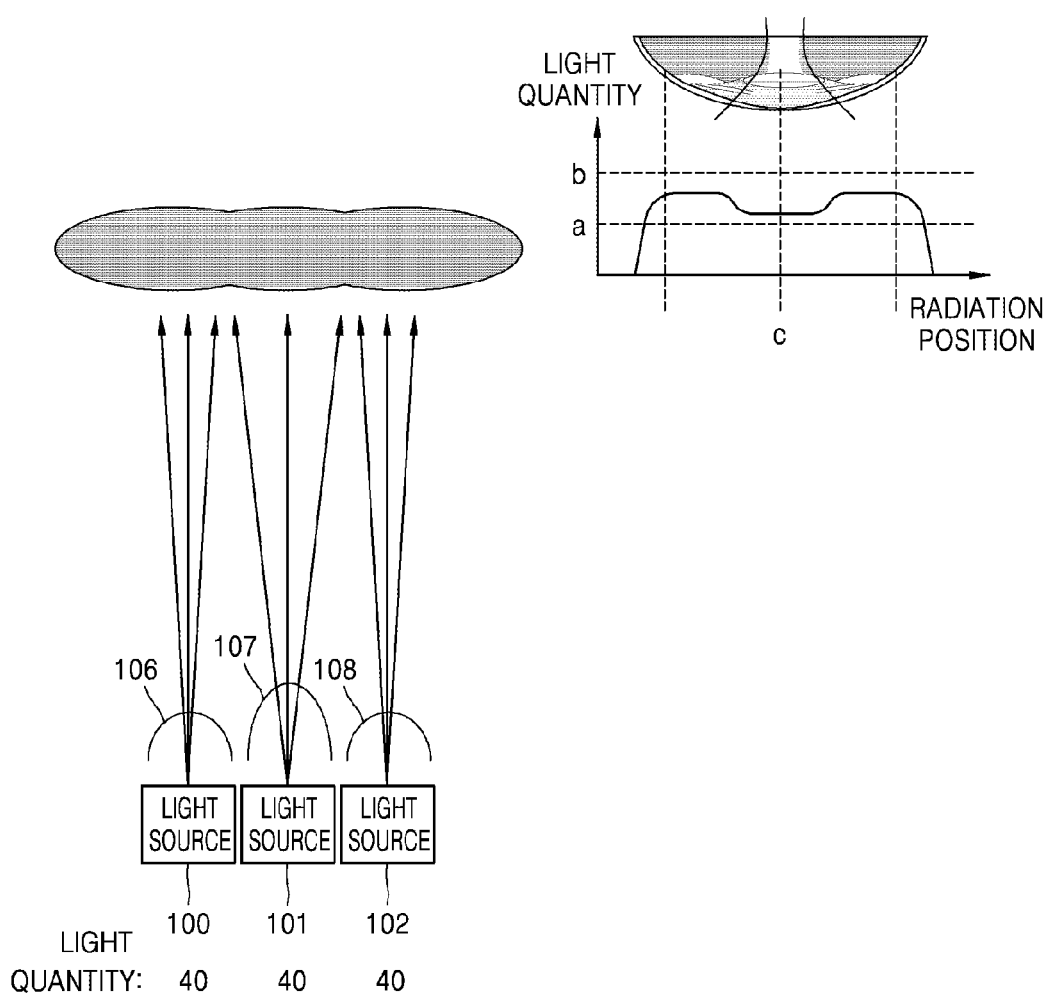
FIG. 10 is a diagram illustrating an example in which light radiated into an iris of a user is adjusted by changing a refractive index in a lens array according to various embodiments of the present disclosure.

FIG. 10 is a diagram illustrating an example in which light radiated into an iris of a user is adjusted by changing a refractive index in a lens array according to some embodiments of the present disclosure.

Referring to FIG. 10, the device may adjust refractive indices of the lenses 106, 107, and 108 included in a lens array to radiate a predetermined quantity of light into an iris. For example, the device may adjust the refractive index of the lens 107 corresponding to a region closer to the central region of the iris to be greater than the refractive indices of the lenses 106 and 108 corresponding to regions further from the central region of the iris. Thus, light radiated from a light source 101 through the lens 107 may be widely dispersed, and at least some of the light radiated from the light source 100, the light radiated from the light source 101, and the light radiated from the light source 102 may overlap one another. Accordingly, light in a relatively uniform quantity ranging between light quantity a and light quantity b may be radiated into the iris. Specifically, the quantity of light radiated around radiation position c is somewhat smaller and between light quantity a and light quantity b.

For example, if the lens 107 is a membrane lens, a reflective index of the lens 107 may be changed by changing a pressure applied to a thin film of the lens 107.

For example, if the lens 107 is an electrowetting lens, the reflective index of the lens 107 may be changed by changing the shape of a boundary surface between two fluids. The device may change the curvature of the boundary source between the two fluids by applying a predetermined voltage to fluids forming the lens 107 and may change the refractive index of the lens 107.

For example, if the lens 107 is a liquid crystal lens, the device may adjust positions and directions of the materials inside the lens 107 by applying a predetermined voltage to materials in the lens and thus may adjust the reflective index of the lens 107.

Figure 11A:
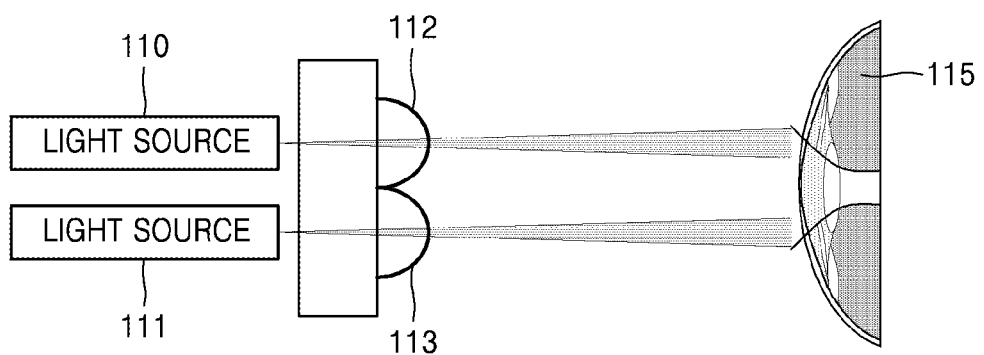
FIGS. 11A and 11B are diagrams illustrating an example in which lenses in a lens array are moved according to various embodiments of the present disclosure.
Figure 11B:
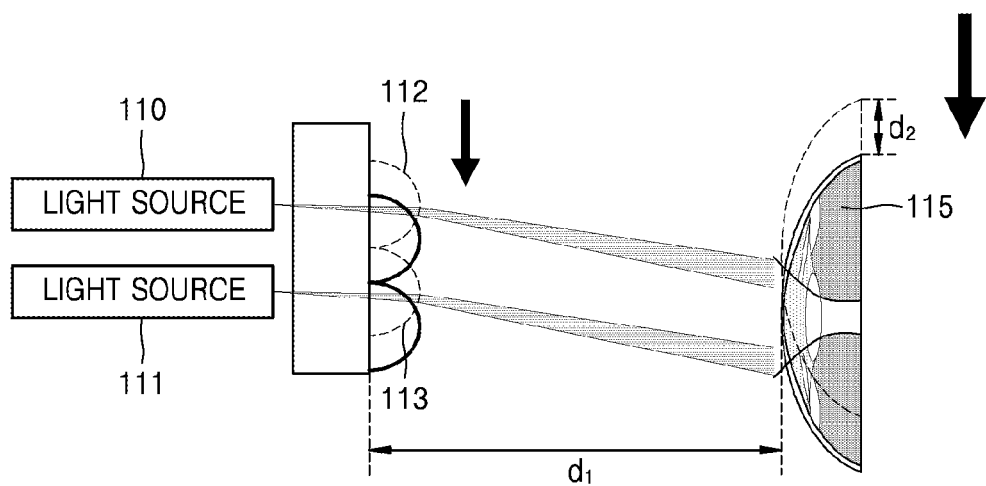

FIGS. 11A and 11B are diagrams illustrating an example in which lenses in a lens array are moved according to various embodiments of the present disclosure.

Referring to FIG. 11A, light sources 110 and 111 may radiate light into an iris 115 through lenses 112 and 113, respectively. Referring to FIG. 11B, a position of the iris 115 may be moved, and the device may move positions of the lens 112 and the lens 113. The device may detect a relative change in positions between the device and the iris and may uniformly move the lens 112 and the lens 113 on the basis of a direction in which and a distance by which the positions are changed.

For example, the device may determine moving directions and moving distances of the lens 112 and the lens 113 on the basis of at least one of a refractive index of the lens 112, a refractive index of the lens 113, a distance $d_1$ between the lens 112 or 113 and the iris of the user, a moving direction of the iris 115, and a moving distance $d_2$ of the iris 115. For example, the moving directions of the lens 112 and the lens 113 are the same as the moving direction of the iris 115. For example, the moving distance of the lens 112 and the lens 113 are the same as the moving distance of the iris 115. However, embodiments of the present disclosure are not limited thereto, and the moving directions and the moving distances of the lens 112 and the lens 113 may be determined using various algorithms.

In addition, the device may determine the moving distances on the basis of the quality of a captured iris image. When some or all of the iris information is not effectively extracted from the captured iris image, the device may determine the moving distances of the lens 112 and the lens 113 according to a predetermined criterion and then move the lens 112 and the lens 113 according to the determined moving distances. For example, when it is difficult to effectively compare the iris information extracted from the captured iris image with predetermined iris information of the user, the device may determine the moving distances of the lens 112 and the lens 113 and then move the lens 112 and the lens 113 according to the determined moving distances. In addition, for example, the device may determine the moving distances of the lens 112 and the lens 113 according to a predetermined criterion such that at least one of brightness, chroma, and hue of the iris image satisfies a predetermined condition. However, embodiments of the present disclosure are not limited thereto.

In addition, for example, the moving directions and the moving distances of the lens 112 and the lens 113 may be determined on the basis of movement of the head of the user or movement of the iris of the user. For example, the device may move the lens 112 and the lens 113 in real time according to the head or iris of the user. In this case, the device may determine the moving directions and the moving distances of the lens 112 and the lens 113 in consideration of a moving direction and a moving distance of the head or iris of the user. In addition, for example, when the iris of the user moves within a predetermined region (e.g., the iris shakes within the predetermined region), the device may determine the moving directions and the moving distances of the lens 112 and the lens 113 such that light may be comparatively uniformly radiated to the predetermined region.

At least one of the quantity of light radiated from the light source 110, the quantity of light radiated from the light source 111, the refractive index of the lens 112, and the refractive index of the lens 113 may be changed according to at least one of the distance between the lens 112 or 113 and the iris of the user, a distance $d_2$ traveled by the iris 115, quality of a captured iris image, and movement of the iris.

FIGS. 12A, 12B, 12C, and 12D are diagrams illustrating an example in which lenses in a lens array are moved using an electrode according to various embodiments of the present disclosure.

Figure 12A:
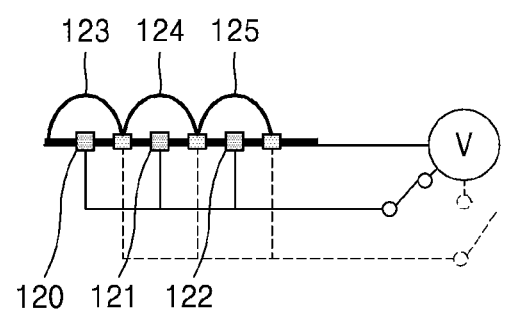
FIGS. 12A, 12B, 12C and 12D are diagrams illustrating an example in which lenses in a lens array are moved using an electrode according to various embodiments of the present disclosure.
Figure 12B:
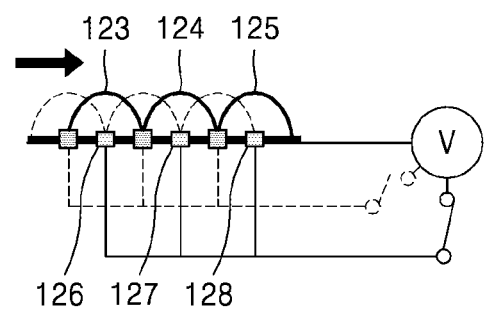

In addition, as shown in FIGS. 12A and 12B, lenses 123, 124, and 125 may be moved in the same direction.

Referring to FIG. 12A, a voltage is applied to electrodes 120, 121, and 122. Thus, a lens 123 may be positioned in the vicinity of the electrode 120, a lens 124 may be positioned in the vicinity of the electrode 121, and a lens 125 may be positioned in the vicinity of the electrode 122. Alternatively, the lens 123 may be formed around the electrode 120, the lens 124 may be formed around the electrode 121, and the lens 125 may be formed around the electrode 122. However, embodiments of the present disclosure are not limited thereto.

Referring to FIG. 12B, a voltage is applied to the electrodes 126, 127, and 128. Thus, the lenses 123, 124, and 125 may be moved. The lens 123 may move to the vicinity of the electrode 126, the lens 124 may move to the vicinity of the electrode 127, and the lens 125 may move to the vicinity of the electrode 128. Alternatively, the lens 123 may be formed around the electrode 126, the lens 124 may be formed around the electrode 127, and the lens 125 may be formed around the electrode 128. However, embodiments of the present disclosure are not limited thereto.

Figure 12C:
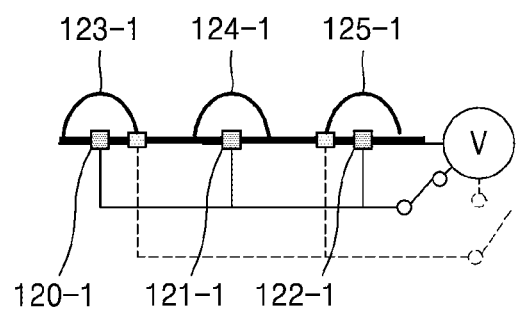
Figure 12D:
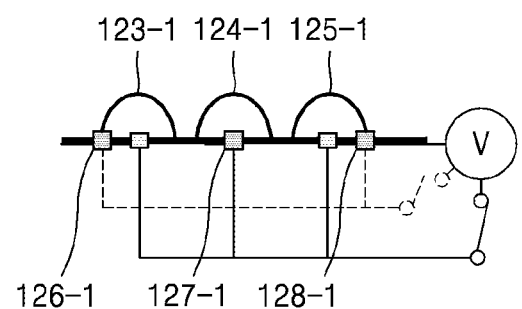

In addition, as shown in FIGS. 12C and 12D, an interval between lenses 123-1 and 124-1 and between lenses 124-1 and 125-1 may be adjusted.

Referring to FIG. 12C, a voltage is applied to electrodes 120-1, 121-1, and 122-1. Thus, a lens 123-1 may be positioned in the vicinity of the electrode 120-1, a lens 124-1 may be positioned in the vicinity of the electrode 121-1, and a lens 125-1 may be positioned in the vicinity of the electrode 122-1. Alternatively, the lens 123-1 may be formed around the electrode 120-1, the lens 124-1 may be formed around the electrode 121-1, and the lens 125-1 may be formed around the electrode 122-1.

Referring to FIG. 12D, a voltage is applied to electrodes 126-1, 127-1, and 128-1. Thus, the lenses 123-1, 124-1, and 125-1 may be moved. The lens 123-1 may move to the vicinity of the electrode 126-1, the lens 124-1 may move to the vicinity of the electrode 127-1, and the lens 125-1 may move to the vicinity of the electrode 127-1. Alternatively, the lens 123-1 may be formed around the electrode 126-1, the lens 124-1 may be formed around the electrode 127-1, and the lens 125-1 may be formed around the electrode 128-1.

However, movements of the lenses forming the lens array are not limited to FIGS. 12A, 12B, 12C, and 12D, and the lenses forming the lens array may be moved to various distances in various directions according to a predetermined criterion.

Figure 13A:
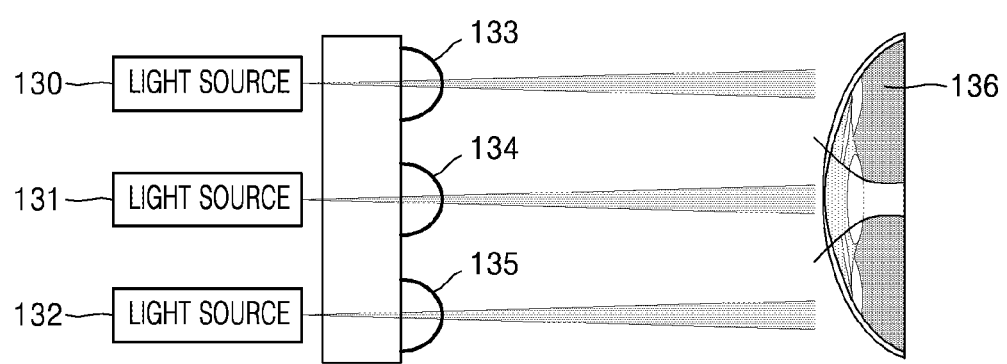
FIGS. 13A and 13B are diagrams illustrating an example in which light radiated from a light source is focused by adjusting an interval between lenses in a lens array according to various embodiments of the present disclosure.
Figure 13B:
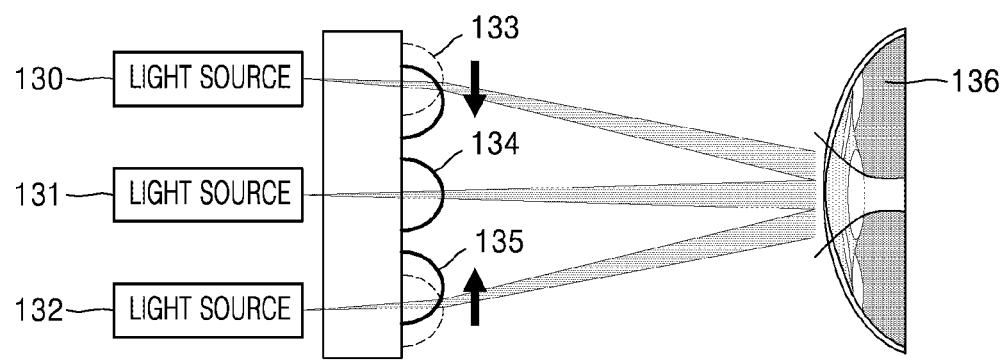

FIGS. 13A and 13B are diagrams illustrating an example in which light radiated from a light source is focused by adjusting an interval between lenses in a lens array according to various embodiments of the present disclosure.

Referring to FIG. 13A, light sources 130, 131, and 132 may radiate light into an iris 136 through lenses 133, 134, and 135, respectively. Referring to FIG. 13B, as the iris moves farther from the light sources 130, 131, and 132, the device may move positions of the lenses 133 and 135. The device may measure a variation in the distance between the device and the iris and move the lenses 133 and 135 in a direction of the lens 134 on the basis of the measured variation in the distance. For example, in a similar manner to that depicted in FIGS. 12A, 12B, 12C, and 12D, the device may apply a voltage to a predetermined electrode to move the lenses 133 and 135 in the direction of the lens 134. Thus, the light radiated from the light sources 130, 131, and 132 may be focused, and a range of the focused light may be increased.

Figure 14A:
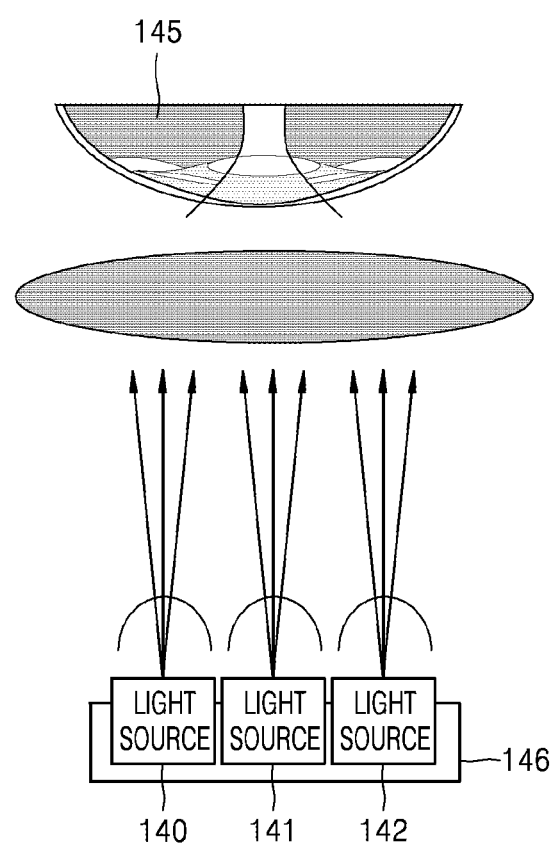
FIGS. 14A and 14B are diagrams illustrating an example in which a range of light radiated from a light source is increased by changing an radiation direction of the light according to various embodiments of the present disclosure.
Figure 14B:
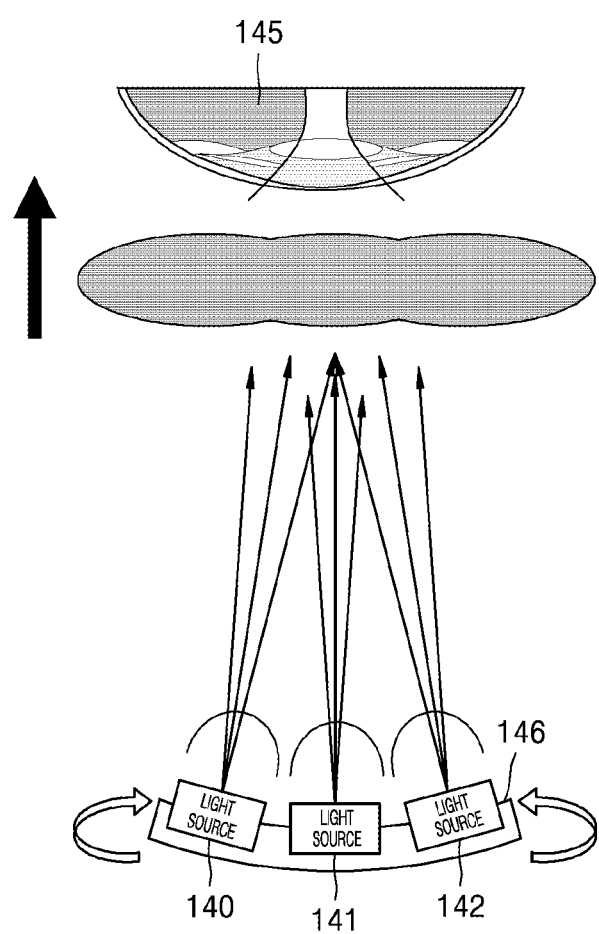

FIGS. 14A and 14B are diagrams illustrating an example in which a range of light radiated from a light source is increased by changing a radiation direction of the light according to various embodiments of the present disclosure.

Referring to FIG. 14A, light sources 140, 141, and 142 may radiate light into an iris 145. Referring to FIG. 14B, the iris 145 may become further apart from the light sources 140, 141, and 142, and thus the device may rotate the light sources 140 and 142 in a direction of the light source 141. For example, the device may rotate the light source 140 in a clockwise direction and may rotate the light source 142 in a counterclockwise direction. Thus, directions of light radiated from the light sources 140 and 142 may be changed. In addition, light radiated from the light source 140, light radiated from the light source 141, and light radiated from the light source 142 may be focused, and a range of the light radiated from the light sources 140, 141, and 142 may be increased.

In addition, referring to FIGS. 14A and 14B, the light sources 141 and 142 may be attached to a predetermined plate 146, and the radiation directions of the light sources 140, 141, and 142 may be changed by bending the plate 146. In this case, the plate 146 may be formed of a flexible material, and the device may bend the plate 146 by applying a predetermined electric signal to the plate 146.

FIGS. 15, 16, 17, and 18 are diagrams illustrating an example in which a light source radiates a plurality of light beams according to various embodiments of the present disclosure.

Figure 15:
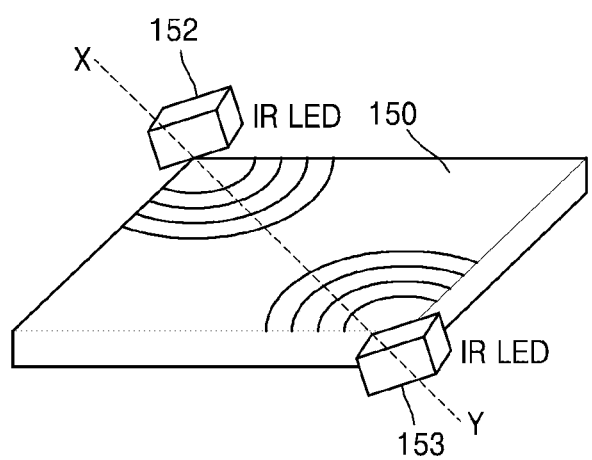
FIGS. 15, 16, 17, and 18 are diagrams illustrating an example in which a light source radiates a plurality of light beams according to various embodiments of the present disclosure.

Referring to FIG. 15, light sources 152 and 153 may radiate light to a plane lens 150 including a plurality of triangular pin lenses. The light sources 152 and 153 may be disposed around two vertices facing each other in a diagonal direction among four vertices of the plane lens 150. In addition, the light source 152 may radiate light in a direction of the light source 153, and the light source 153 may radiate light in a direction of the light source 152. The light radiated from the light source 152 and the light radiated from the light source 153 may be dispersed by a plurality of triangular pin lenses in the plane lens 150. The dispersed light may be radiated into an iris of a user.

Figure 16:
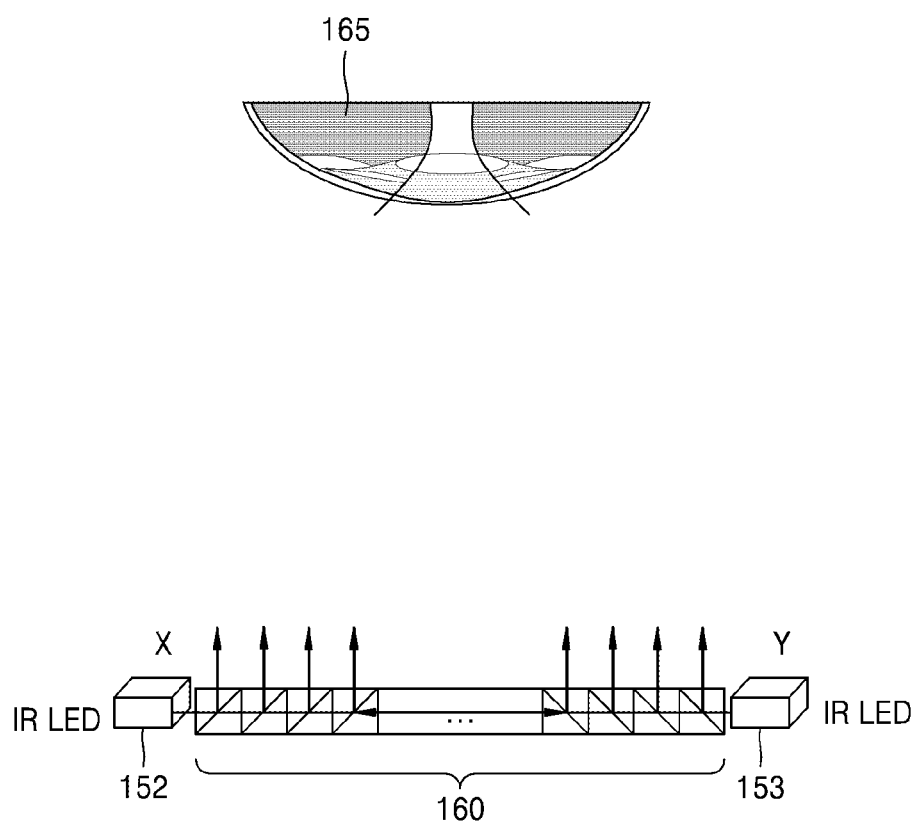

Referring to FIG. 16, a plurality of triangular pin lenses 160 may be arranged along a line connecting the light source 152 and the light source 153. In addition, the light source 152 may radiate light toward the light source 153 via the triangular pin lenses 160, and the light source 153 may radiate light toward the light source 152 via the triangular pin lenses 160.

In addition, a portion of the light radiated from the light source 152 may be transmitted through the triangular pin lenses 160, and the remaining portion of the light radiated from the light source 152 may be reflected by the triangular pin lenses 160. In addition, a portion of the light radiated from the light source 153 may be transmitted through the triangular pin lenses 160, and the remaining portion of the light radiated from the light source 153 may be reflected by the triangular pin lenses 160.

The light reflected by the triangular pin lenses 160 may be radiated into an iris 165 of the user. In addition, the light reflected by the triangular pin lenses 160 may have relatively uniform quantities by adjusting characteristics (e.g., transparency) of the triangular pin lenses 160.

In addition, a lens array may be disposed between the plane lens including the triangular pin lenses 160 and the iris 165, but is not limited thereto.

Figure 17:
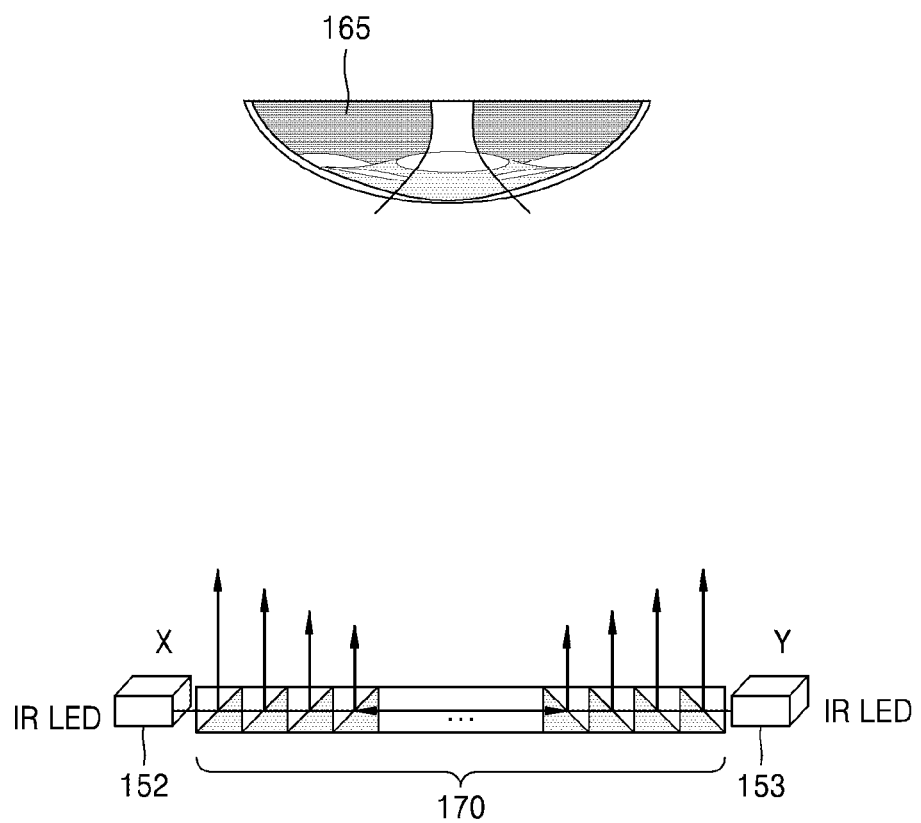

Referring to FIG. 17, a plurality of triangular pin lenses 170 may be arranged along a line connecting the light source 152 and the light source 153. In addition, the light source 152 may radiate light toward the light source 153 via the triangular pin lenses 170, and the light source 153 may radiate light toward the light source 152 via the triangular pin lenses 170.

In addition, a portion of the light radiated from the light source 152 may be transmitted through the triangular pin lenses 170, and the remaining portion of the light radiated from the light source 152 may be reflected by the triangular pin lenses 170. In addition, a portion of the light radiated from the light source 153 may be transmitted through the triangular pin lenses 170, and the remaining portion of the light radiated from the light source 153 may be reflected by the triangular pin lenses 170.

The light reflected by the triangular pin lenses 170 may be radiated into the iris 165 of the user. In addition, the device may gradually decrease the quantity of light transmitted through the triangular pin lenses 170 by adjusting characteristics (e.g., transparency) of the triangular pin lenses 170. Thus, the device may set the quantity of light reflected by a triangular pin lens positioned further from the light sources 152 and 153 to be smaller than the quantity of light reflected by a triangular pin lens positioned closer to the light sources 152 and 153.

In addition, a lens array may be disposed between the plane lens including the triangular pin lenses 170 and the iris 165, but is not limited thereto.

Figure 18:
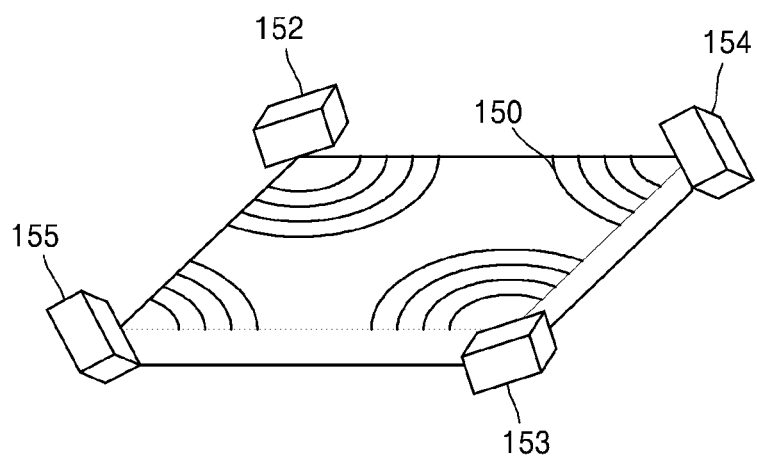

Referring to FIG. 18, light sources 152, 153, 154, and 155 may radiate light to a plane lens 150 including a plurality of triangular pin lenses. The light sources 152, 153, 154, and 155 may be disposed around four vertices of the plane lens 150. In addition, the light source 152 may radiate light in a direction of the light source 153, the light source 153 may radiate light in a direction of the light source 152, the light source 154 may radiate light in a direction of the light source 155, and the light source 155 may radiate light in a direction of the light source 154. The light radiated from the light source 152, the light radiated from the light source 153, the light radiated from the light source 154, and the light radiated from the light source 155 may be dispersed by a plurality of triangular pin lenses in the plane lens 150. The dispersed light may be radiated into an iris of a user.

Figure 19:
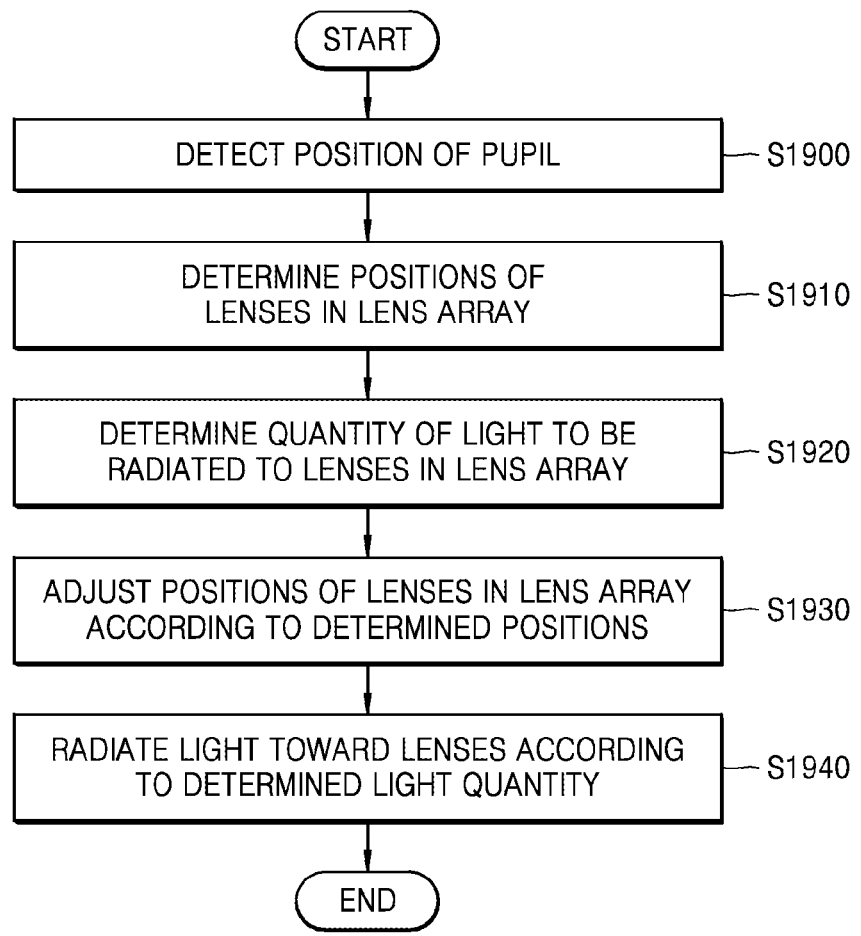
FIG. 19 is a flowchart of a method for adjusting light radiated into an iris according to various embodiments of the present disclosure.

FIG. 19 is a flowchart of a method for adjusting light radiated into an iris according to some embodiments of the present disclosure.

Referring to FIG. 19, in operation S1900, the device may detect a position of a pupil. The device may capture a pupil of a user using a camera included in the device and detect a position of the pupil on the basis of the captured image. In addition, the device may calculate a distance from the device to the iris on the basis of the captured image. For example, the device may calculate a distance from the lens to the iris. In this case, the device may calculate a relative distance value (i.e., a distance index) between the device and the iris of the user on the basis of the size of the pupil of the user included in the captured image.

The device may detect the pupil from the captured iris image and calculate a distance from the device to the iris from a size of the detected pupil. When the size of the detected pupil is larger, the device may determine that the distance from the device to the iris of the user is smaller. When the size of the detected pupil is smaller, the device may determine that the distance from the device to the iris of the user is greater. The device may calculate the distance from the device according to a predetermined criterion on the basis of the size of the detected pupil.

In addition, the device may determine the distance from the device to the iris of the user using a TOF camera included in the device. The device may radiate light into the iris of the user and receive light reflected from the iris of the user. For example, the device may control the TOF camera to radiate light emitted from a light source of the TOF camera into the iris of the user and receive light reflected from the iris. In addition, the device may use a phase difference between the radiated light and the reflected light to calculate the distance between the device and the iris of the user.

However, the method for measuring the distance between the device and the iris of the user is not limited thereto. For example, the device may use various sensors, such as an infrared sensor and an ultrasonic sensor, to measure the distance between the device and the iris of the user.

In addition, the device may determine a relative position and direction of the iris with respect to the device on the basis of the captured image. The device may determine the relative position and direction of the pupil with respect to the device on the basis of the position of the pupil in the captured image. The device may detect the position of the pupil at predetermined periods. In addition, the device may detect the position of the pupil when a predetermined event occurs.

In operation S1910, the device may determine positions of lenses in a lens array. The device may determine the positions of the lenses in the lens array on the basis of the distance between the device and the iris. As the distance between the device and the iris becomes larger, the device may reduce the interval in the lens array. The device may determine the positions of the lenses in consideration of the quantity of light to be radiated to the lenses.

In addition, the device may determine the positions of the lenses in the lens array to uniformly move the lenses on the basis of the relative position of the iris with respect to the device. For example, as illustrated above with reference to FIGS. 11A and 11B, the device may determine the positions of the lenses in the lens array to move the lenses the same distance in the same direction.

In addition, a criterion for determining the positions of the lenses may be predetermined and may be set in consideration of, for example, the distance between the device and the iris, the relative position of the iris with respect to the device, the intensity of light radiated to the lenses, and refractive indices of the lenses. The device may determine moving directions and the moving distances of the lenses included in the lens array on the basis of at least one of, for example, the refractive indices of the lenses included in the lens array and the distances from the lenses into the iris of the user.

In addition, when the user moves, and thus the iris of the user moves, the device may determine the moving directions and the moving distances of the lenses included in the lens array in consideration of a moving direction and a moving distance of the iris.

In addition, the device may determine the positions of the lenses in the lens array according to quality of the iris image. When some or all of the iris information is not effectively extracted from the captured iris image, the device may determine the moving directions and the moving distances of the lenses in the lens array. The device may determine the moving directions and the moving distances of the lenses in the lens array such that an iris image for a part of the entire iris region from which the iris information is not effectively extracted may be effectively captured.

In addition, when the iris is moved with movement of the user, the device may adjust the quantity of light radiated to the lenses in the lens array on the basis of the moving direction and the moving distance of the iris.

In addition, the light that has passed through the lenses is combined and then reaches the iris, and the criterion for determining the positions of the lenses may be determined such that the quantity of the combined light that has reached the iris may be included in a predetermined range over the entire are of the iris.

In operation S1920, the device may determine the quantity of light to be radiated to the lenses in the lens array. The device may determine the quantity of light to be radiated to the lenses in the lens array on the basis of the position of the iris. In addition, the device may determine the quantity of light to be radiated to the lenses in the lens array on the basis of the calculated distance. As the distance between the device and the iris becomes larger, the device may increase the quantity of light to be radiated to the lens.

In addition, the controller may determine the quantity of light to be different for each lens in the lens array. For example, the device may set the quantity of light to be radiated to a lens corresponding to a central region of the iris to be smaller and may set the quantity of light to be radiated to a lens corresponding to a region further from the central region to be larger.

In addition, a criterion for determining the quantity of light to be radiated to the lenses may be predetermined and may be set in consideration of, for example, the distance between the device and the iris, the relative position of the iris with respect to the device, positions of the lenses with respect to the light source and the iris, and refractive indices of the lenses. In addition, the light that has passed through the lenses is combined and then reaches the iris, and the criterion for determining the quantity of light to be radiated to the lenses may be determined such that the quantity of the combined light that has reached the iris may be included in a predetermined range over the entire area of the iris.

In addition, the device may determine the quantity of light radiated to the lenses in the lens array according to quality of the iris image. When some or all of the iris information is not effectively extracted from the captured iris image, the device may determine the quantity of light to be radiated to the lenses in the lens array. The device may determine the quantity of light radiated to the lenses in the lens array such that more light may be radiated to a part of the entire iris area in which the iris information is not effectively extracted.

In addition, when the iris is moved due to movement of the user, the device may adjust the quantity of light radiated to the lenses in the lens array on the basis of the moving direction and the moving distance of the iris.

In operation S1930, the device may adjust the positions of the lenses in the lens array according to the determined positions. The device may move the lenses in the lens array according to the positions determined in operation S1910.

A plurality of electrodes may be positioned in the lens array, and the device may apply a voltage to some of the plurality of electrodes to move the lenses. The lenses may be moved to regions including points at which the electrodes to which the voltage is applied are positioned. Alternatively, the device may move the lenses by moving a plate in which the lens array is formed. However, embodiments of the present disclosure are not limited thereto.

In operation S1940, the device may radiate light to the lenses according to the determined quantity of light. The device may use a plurality of light sources corresponding to the lenses to radiate light to the lenses. Alternatively, the device may use a plane lens including a plurality of triangular pin lenses to disperse light radiated from a light source and radiate the dispersed light to the lenses. However, embodiments of the present disclosure are not limited thereto.

Figure 20:
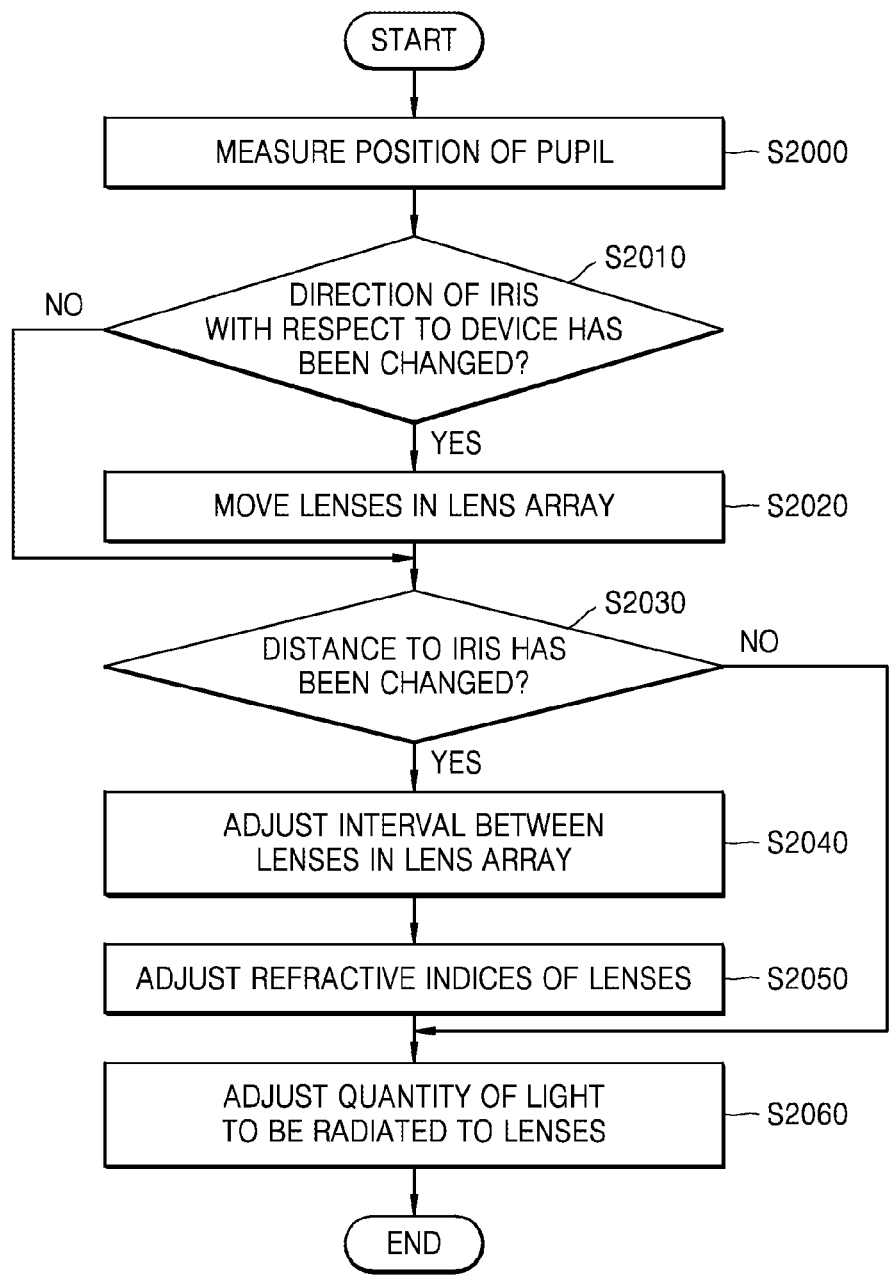
FIG. 20 is a flowchart of a method for moving lenses included in a lens array and adjusting the quantity of light radiated from a light source according to various embodiments of the present disclosure.

FIG. 20 is a flowchart of a method for moving lenses included in a lens array and adjusting the quantity of light radiated from a light source according to various embodiments of the present disclosure.

Referring to FIG. 20, in operation S2000, the device may measure a position of an iris of a user. The device may capture a pupil of the user using a camera included in the device and detect a position of the pupil on the basis of the captured image. In addition, the device may calculate a distance from the device to an iris on the basis of the captured image. In this case, the device may calculate a relative distance value (i.e., a distance index) between the device and the iris of the user on the basis of the size of the pupil of the user included in the captured image. In addition, the device may determine a relative position and direction of the iris with respect to the device on the basis of the captured image. The device may determine the relative position and direction of the pupil with respect to the device on the basis of the position of the pupil in the captured image. The device may detect the position of the pupil at predetermined periods. In addition, the device may detect the position of the pupil when a predetermined event occurs.

In operation S2010, the device may determine whether the direction of the iris with respect to the device has been changed. When the device moves or the face of the user moves, the relative position between the device and the iris may be changed, and thus the direction of the iris with respected to the device may be changed as shown in FIGS. 11A and 11B.

When the direction of the iris with respect to the device is determined to have been changed as a result of the determination in operation S2010, the device may move the lenses in the lens array in operation S2020. The device may move the lenses in the lens array such that light radiated from a light source may reach the moved iris. For example, the device may move the lenses in the lens array the same distance in the same direction to uniformly move the lens array. The device may determine moving distances by which and directions in which the lenses are to be moved, according to how far the iris is moved in a direction horizontal to the device.

A plurality of electrodes may be arranged on a surface of the lens array, and the device may apply a voltage to some of the plurality of electrodes to move the lenses. The lenses may be moved to regions including the electrodes to which the voltage is applied. Alternatively, a lens may be formed in the regions including the electrodes to which the voltage is applied. In addition, the device may move the lenses in the lens array by moving a plate of the lens array. However, embodiments of the present disclosure are not limited thereto.

In operation S2030, the device may determine whether the distance between the device and the iris has been changed. When the device moves or the face of the user moves, the relative position between the device and the iris may be changed, and thus the distance from the device to the iris may be changed.

When the distance between the device and the iris is determined to have been changed as a result of the determination in operation S2030, the device may adjust an interval between lenses in the lens array in operation S2040. As the distance between the device and the iris becomes larger, the device may reduce the interval in the lens array. On the other hand, as the distance between the device and the iris becomes smaller, the device may increase the interval in the lens array. In addition, the device may adjust the interval between the lenses in consideration of the quantity of light to be radiated to the lens.

In operation S2050, the device may adjust refractive indices of the lenses in the lens array. The device may adjust the refractive indices of the lenses included in the lens array in order to radiate a relatively uniform quantity of light into the iris. For example, the device may adjust the refractive index of the lens corresponding to a region closer to the central region of the iris to be greater than the refractive index of the lens corresponding to a region further from the central region of the iris. For example, if the lens is a membrane lens, a reflective index of the lens may be changed by changing a pressure applied to a thin film of the lens. For example, if the lens is an electrowetting lens, the reflective index of the lens may be changed by changing the shape of a boundary surface between two fluids. The device may change the curvature of the boundary source between the two fluids by applying a predetermined voltage to fluids forming the lens and thus may change the refractive index of the lens. In addition, if the lens is a liquid crystal lens, the device may adjust positions and directions of the materials constituting the liquid crystal inside the lens by applying a predetermined voltage to materials constituting a liquid crystal included in the lens and thus may adjust the reflective index of the lens.

In operation S2060, the device may adjust the quantity of light to be radiated to the lenses in the lens array. The device may adjust the quantity of light to be radiated to the lenses included in the lens array, according to how further the iris is moved in a direction horizontal to the device. In addition, the device may adjust the quantity of light to be radiated to the lenses in the lens array on the basis of the distance from the device to the iris.

Some embodiments of the present disclosure may be implemented as a recording medium including instructions executable by a computer such as a program module executed by the computer. A computer-readable medium may be any usable medium accessible by a computer and may include volatile and non-volatile media and discrete and integrated media. Also, the computer-readable medium may include both a computer storage medium and a communication medium. The computer storage medium includes the volatile and non-volatile media and the discrete and integrated media, which are implemented in any method or technique for storing information such as a computer readable instruction, data structure, program module, or other data. The communication module typically includes the computer readable instruction, data structure, program module, or other data and transmission mechanism of a modulated data signal such as a carrier and further includes any information transmission medium.

In this disclosure, the term "unit" may denote a hardware component such as a processor or circuit or a software component executed by the hardware component such as a processor.

The above description is merely illustrative, and it will be understood by those skilled in the art that various changes in form and details may be made therein without departing from the spirit and scope of the disclosure as defined by the appended claims. The above embodiments of the present disclosure are accordingly to be regarded as illustrative rather than restrictive. For example, while a single element may be distributed and then carried out, distributed elements may be carried out in a combination thereof.

While the present disclosure has been shown and described with reference to various embodiments thereof, it will be understood by those skilled in the art that various changes in form and details may be made therein without departing from the spirit and scope of the present disclosure as defined by the appended claims and their equivalents.

What is claimed is:

1. A mobile device for radiating light to capture an iris of a user, the mobile device comprising:
   a lens unit including a lens array of arranged lenses;
   a light source configured to radiate light beams into the iris of the user via the arranged lenses by emitting the light beams toward the arranged lenses; and
   at least one processor configured to change positions of the arranged lenses based on a distance between the mobile device and the iris, the changing of the positions of the arranged lenses comprising:
   sensing movement of the iris, and
   moving the arranged lenses based on the movement of the iris,
   wherein the lens array is positioned between the light source and the iris, and
   wherein movement directions of the arranged lenses are determined based on a movement direction of the iris.

2. The mobile device of claim 1, further comprising a camera configured to capture an image of the iris of the user, wherein the at least one processor is further configured to use the captured image of the iris to calculate the distance between the mobile device and the iris.

3. The mobile device of claim 1, wherein the at least one processor is further configured to adjust an interval between the arranged lenses according to the distance between the mobile device and the iris.

4. The mobile device of claim 1, wherein the at least one processor is further configured to focus the light beams emitted from the light source by decreasing the interval between the arranged lenses.

5. The mobile device of claim 1, wherein the at least one processor is further configured to calculate the distance between the mobile device and the iris based on a direction perpendicular to the mobile device.

6. The mobile device of claim 1, wherein the at least one processor is further configured to set a quantity of first light beams to be radiated toward a lens corresponding to a central region of the iris to be less than a quantity of second light beams to be radiated toward a lens corresponding to a peripheral region of the iris.

7. The mobile device of claim 1, wherein the at least one processor is further configured to:
   determine a moving direction and a moving distance of the iris based on a direction horizontal to the mobile device, and
   move the arranged lenses the same distance in the same direction based on the determined moving direction and moving distance.

8. The mobile device of claim 1, wherein the at least one processor is further configured to change the positions of the arranged lenses by applying a voltage to electrodes arranged in the lens array.

9. The mobile device of claim 1,
   wherein the light beams that are emitted from the light source and transmitted through the arranged lenses overlap one another, and
   wherein the overlapped light beams include a quantity within a predetermined range and are radiated to an entire area of the iris.

10. A method of radiating light from a mobile device to capture an iris of a user, the method comprising:
    determining a distance between the mobile device and the iris;

changing positions of arranged lenses forming a lens array based on the determined distance, the changing of the positions of the arranged lenses comprising:
sensing movement of the iris, and
moving the arranged lenses based on the movement of the iris; and
emitting light beams toward the arranged lenses,
wherein the lens array is positioned between a light source and the iris, and the emitted light beams reach the iris of the user via the arranged lenses, and
wherein movement directions of the arranged lenses are determined based on a movement direction of the iris.

11. The method of claim 10, further comprising capturing an image of the iris of the user,
wherein the determining of the distance comprises using the captured image of the iris to calculate the distance between the mobile device and the iris.

12. The method of claim 10, wherein the changing of the positions of the arranged lenses comprises adjusting an interval between the arranged lenses according to the distance between the mobile device and the iris.

13. The method of claim 10, wherein the changing of the positions of the arranged lenses comprises decreasing an interval between the arranged lenses wherein the light beams emitted from the light sources are transmitted through the arranged lenses having the decreased interval and thus focused.

14. The method of claim 10, wherein the determining of the distance between the mobile device and the iris comprises calculating the distance between the mobile device and the iris based on a direction perpendicular to the mobile device.

15. The method of claim 10, further comprising setting a quantity of the light beams to be radiated toward the lenses,
wherein a quantity of first light beams to be radiated toward a lens corresponding to a central region of the iris is set to be less than a quantity of second light beams to be radiated toward a lens corresponding to a peripheral region of the iris.

16. The method of claim 10, wherein the changing of the positions of the arranged lenses comprises:
determining a moving direction and a moving distance of the iris based on a direction horizontal to the mobile device; and
moving the arranged lenses the same distance in the same direction based on the determined moving direction and moving distance.

17. The method of claim 10, wherein the changing of the positions of the arranged lenses comprises changing the positions of the arranged lenses forming the lens array by applying a voltage to electrodes arranged in the lens array.

18. A non-transitory computer-readable recording medium storing a computer program for executing the method of claim 10.

* * * * *